(12) United States Patent
Wu et al.

(10) Patent No.: US 11,551,804 B2
(45) Date of Patent: Jan. 10, 2023

(54) ASSISTING PSYCHOLOGICAL CURE IN AUTOMATED CHATTING

(71) Applicant: MICROSOFT TECHNOLOGY LICENSING, LLC, Redmond, WA (US)

(72) Inventors: Xianchao Wu, Redmond, WA (US); Zhan Chen, Redmond, WA (US); Di Li, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 103 days.

(21) Appl. No.: 16/612,742

(22) PCT Filed: May 11, 2017

(86) PCT No.: PCT/CN2017/083941
§ 371 (c)(1),
(2) Date: Nov. 11, 2019

(87) PCT Pub. No.: WO2018/205224
PCT Pub. Date: Nov. 15, 2018

(65) Prior Publication Data
US 2020/0082928 A1    Mar. 12, 2020

(51) Int. Cl.
*G16H 20/70* (2018.01)
*G16H 10/60* (2018.01)
(Continued)

(52) U.S. Cl.
CPC ............. *G16H 20/70* (2018.01); *G16H 10/20* (2018.01); *G16H 10/60* (2018.01); *G16H 50/20* (2018.01);
(Continued)

(58) Field of Classification Search
None
See application file for complete search history.

(56) References Cited

U.S. PATENT DOCUMENTS 6,731,307 B1    5/2004  Strubbe
2001/0034615 A1 10/2001 Wilkinson et al.
(Continued)

FOREIGN PATENT DOCUMENTS

CA    2966962 A1    5/2016
CN  105912846 A    8/2016
(Continued)

OTHER PUBLICATIONS

Danisman, Taner and Adil Alpkocak. "Feeler: Emotion Classification of Text Using Vector Space Model." (2008) http://citeseerx.ist.psu.edu/viewdoc/download?doi=10.1.1.189.3795&rep=rep1&type=pdf (Year: 2008).*

(Continued)

*Primary Examiner* — Devin C Hein
(74) *Attorney, Agent, or Firm* — Workman Nydegger

(57) ABSTRACT

Method and apparatus for assisting psychological cure in automated chatting. At least one message may be received in a chat flow, a psychological test may be performed based on the at least one message, and a cure strategy may be provided based at least on the psychological test. A first request for obtaining user information of a user may be received in a chat flow, the user information may be provided based on the first request, a second request for obtaining a suggested cure strategy for the user may be received, and the suggested cure strategy may be provided based on the second request, wherein the suggested cure strategy may be determined based at least on the user information.

20 Claims, 18 Drawing Sheets

(51) Int. Cl.
- *G16H 50/70* (2018.01)
- *G16H 50/20* (2018.01)
- *G16H 10/20* (2018.01)
- *G16H 70/20* (2018.01)
- *G16H 80/00* (2018.01)

(52) U.S. Cl.
CPC ............. *G16H 50/70* (2018.01); *G16H 70/20* (2018.01); *G16H 80/00* (2018.01)

(56) References Cited

U.S. PATENT DOCUMENTS

| | | | |
|---|---|---|---|
| 2009/0144089 A1* | 6/2009 | Heywood | G16H 50/20 705/3 |
| 2011/0151418 A1 | 6/2011 | Delespaul et al. | |
| 2011/0245633 A1 | 10/2011 | Goldberg et al. | |
| 2013/0085758 A1 | 4/2013 | Csoma et al. | |
| 2014/0113263 A1 | 4/2014 | Jarrell et al. | |
| 2014/0249830 A1 | 9/2014 | Gallopyn et al. | |
| 2014/0279050 A1* | 9/2014 | Makar | G06F 16/9535 705/14.66 |
| 2016/0342683 A1 | 11/2016 | Lim et al. | |
| 2017/0004260 A1* | 1/2017 | Moturu | G16H 10/60 |
| 2017/0188976 A1* | 7/2017 | Kalra | G16H 10/20 |
| 2017/0213007 A1* | 7/2017 | Moturu | G16H 20/10 |
| 2018/0145935 A1* | 5/2018 | Blokhin | H04L 51/02 |
| 2018/0218126 A1* | 8/2018 | Salazar | G16H 70/20 |

FOREIGN PATENT DOCUMENTS

| | | |
|---|---|---|
| CN | 106618609 A | 5/2017 |
| KR | 20060108360 A | 10/2006 |
| WO | 2016/201815 A1 | 12/2016 |

OTHER PUBLICATIONS

Tess (X2.AI and https://www.newyorker.com/tech/annals-of-technology/the-chatbot-will-see-you-now) (Year: 2016).*

X2AI. Tess. https://web.archive.org/web/20160406193722/https://x2.ai/#examples, https://web.archive.org/web/20160325180326/X2.AI/exec.pdf, 2016 (Year: 2016).*

International Search Report and Written Opinion for PCT/CN2017/083941, dated Feb. 9, 2018.

Wysa, Retrieved From: http://www.ayushmantalwar.com/wysanew.html, 6 Pages.

"Extended European Search Report Issued in European Patent Application No. 17909161.6", dated Oct. 9, 2020, 10 Pages.

Bickmore et al., "Relational Agents in Clinical Psychiatry", In Journal of Harvard Review of Psychiatry, vol. 18, Issue 2, Mar. 2010, 40 Pages.

Bunardzic, Alex, "Four Types Of Bots", Retrieved From https://chatbotsmagazine.com/four-types-of-bots-432501e79a2f, May 17, 2016, 6 Pages.

Davidson, Jordan, "Facebook Messenger Chatbot, Joy, Wants to Help People Improve Their Mental Health", Retrieved from https://themighty.com/2016/07/facebook-messenger-chatbot-joy-wants-to-help-improve-mental-health/, Jul. 27, 2016, 09 Pages.

Fung et al., "Towards Empathetic Human-Robot Interactions", In International Conference on Intelligent Text Processing and Computational Linguistics, Apr. 3, 2016, 23 Pages.

Kumar et al., "Ask Me Anything: Dynamic Memory Networks for Natural Language Processing", In Journal of Computing Research Repository, Jun. 19, 2015, pp. 1-10.

Robinson, Ann, "Meet Ellie, the machine that can detect depression", Retrieved From: https://www.theguardian.com/sustainable-business/2015/sep/17/ellie-machine-that-can-detect-depression, Sep. 17, 2015, 8 Pages.

"Office Action Issued in Indian Patent Application No. 201917044425", dated Aug. 31, 2021, 6 Pages.

\* cited by examiner

ASSISTING PSYCHOLOGICAL CURE IN AUTOMATED CHATTING

This application is a U.S. National Stage Application of PCT/CN2017/083941, filed May 11, 2017, which application is hereby incorporated by reference. To the extent appropriate, a claim of priority is made to the above disclosed application.

BACKGROUND

Artificial Intelligence (AI) chatbot is becoming more and more popular, and is being applied in an increasing number of scenarios. The chatbot is designed to simulate people's conversation, and may chat with users by text, speech, image, etc. Generally, the chatbot may scan for keywords within a message input by a user or apply natural language processing on the message, and provide a response with the most matching keywords or the most similar wording pattern to the user.

SUMMARY

This Summary is provided to introduce a selection of concepts that are further described below in the Detailed Description. It is not intended to identify key features or essential features of the claimed subject matter, nor is it intended to be used to limit the scope of the claimed subject matter.

Embodiments of the present disclosure propose method and apparatus for assisting psychological cure in automated chatting. In some implementations, at least one message may be received in a chat flow, a psychological test may be performed based on the at least one message, and a cure strategy may be provided based at least on the psychological test. In some implementations, a first request for obtaining user information of a user may be received in a chat flow, the user information may be provided based on the first request, a second request for obtaining a suggested cure strategy for the user may be received, and the suggested cure strategy may be provided based on the second request, wherein the suggested cure strategy may be determined based at least on the user information.

It should be noted that the above one or more aspects comprise the features hereinafter fully described and particularly pointed out in the claims. The following description and the drawings set forth in detail certain illustrative features of the one or more aspects. These features are only indicative of the various ways in which the principles of various aspects may be employed, and this disclosure is intended to include all such aspects and their equivalents.

BRIEF DESCRIPTION OF THE DRAWINGS

The disclosed aspects will hereinafter be described in connection with the appended drawings that are provided to illustrate and not to limit the disclosed aspects.

DETAILED DESCRIPTION

Figure 1:
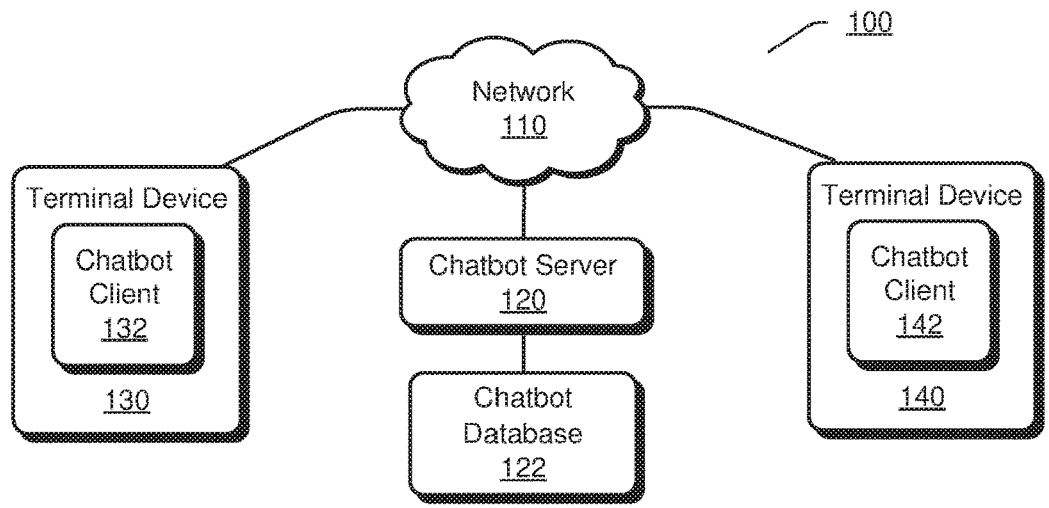
FIG. 1 illustrates an exemplary application scenario of a chatbot according to an embodiment.

The present disclosure will now be discussed with reference to several example implementations. It is to be understood that these implementations are discussed only for enabling those skilled in the art to better understand and thus implement the embodiments of the present disclosure, rather than suggesting any limitations on the scope of the present disclosure.

Usually, it is difficult and essential to capture and evaluate people strong negative emotions when they are facing or experienced hard times with heavy stresses remained in their mind. One fact is that not only young people but also children and adult people may have stresses during their ordinary life. Conventional psychological cure methods cannot detect people strong negative emotions, such as, tendency of suicide, in an automatic and efficient way. This is because that people tend to close their mind to other people and do not want to talk too much in details what they are suffering. Even for close friends, there is still a tendency to pretend to be "happy" to keep their relationship, and to hide individual unhappiness with no one else to talk to. Moreover, change of emotion always comes from small or sudden changes of daily life, and it is difficult to detect these changes "in-time" even for real world psychologists. Furthermore, there are too many people living in the real world, yet the number of qualified psychologists is quite limited, and thus the limited resources of real world psychologists are not sufficient for in-time psychological cure for a great number of people.

The embodiments of the present disclosure propose to use a chatbot to assist psychological cure. Herein, "psychological cure" may refer to psychotherapy, psychological counselling, psychological tests, etc.

Instead of talking to real world people about sufferings or stresses, it is easier for a person to talk to a chatbot with angry words, sad words, dirty words, etc., since the person knows that these words will not actually hurt anybody in the real world. This opens a door for detecting people' negative emotions and further providing a corresponding cure strategy. Herein, "cure strategy" may refer to psychological cure solution, psychological cure suggestion, etc.

As a person talks more and more with a chatbot, an emotion curve across timeline may be generated to better analyze the person's emotional change during a time period. This information may be further used for building a responding cure strategy for the person.

According to the embodiments of the present disclosure, as a result of accumulating large-scale individual person's emotion data and psychological cure strategies, the chatbot may learn how to provide a personalized cure strategy through deep learning techniques. This chatbot may act as a virtual psychologist for users or act as an assistant for psychologists. Hereinafter, "users" may refer to persons chatting with the chatbot and being monitored by the chatbot in terms of psychological conditions. Moreover, hereinafter, "psychologists" may refer to persons using the chatbot for providing psychological cure or salvation, e.g., doctors in a psychological department of a hospital, social workers providing psychological salvation, teachers in schools, etc. The chatbot may become more and more powerful through online training processes, and may assist or even take place of real world psychologists for providing 24-hour psychological services.

The embodiments of the present disclosure further propose a sentiment analysis classifier that takes text, voice, image and video as inputs. The sentiment analysis process may help generating personalized emotion curves and cure strategies.

The embodiments of the present disclosure further propose a Dynamic Memory Network (DMN)-based cure strategy reasoning framework, for generating a cure strategy that is to be provided to a user or a psychologist.

The embodiments of the present disclosure propose user interfaces (UIs) for both users and psychologists. In a UI between the chatbot and a user, the chatbot may chat with the user, collect information of the user, provide cure strategies to the user, introduce a psychologist to provide cure strategies, etc. In a UI between the chatbot and a psychologist, the chatbot may chat with the psychologist, provide information of users, provide suggested cure strategies to the psychologist, introduce a user, etc.

The chatbot according to the embodiments of the present disclosure may assist psychological cure, e.g., performing psychological tests, providing cure strategies, etc. Thus, for example, the chatbot may detect people who are suffering negative emotions, and help preventing these people from taking extreme actions of hurting themselves or other people.

FIG. 1 illustrates an exemplary application scenario 100 of a chatbot according to an embodiment.

In FIG. 1, a network 110 is applied for interconnecting among a chatbot server 120, a terminal device 130 and a terminal device 140.

The network 110 may be any type of networks capable of interconnecting network entities. The network 110 may be a single network or a combination of various networks. In terms of coverage range, the network 110 may be a Local Area Network (LAN), a Wide Area Network (WAN), etc. In terms of carrying medium, the network 110 may be a wireline network, a wireless network, etc. In terms of data switching techniques, the network 110 may be a circuit switching network, a packet switching network, etc.

The terminal device 130 and the terminal device 140 may be any type of electronic computing devices capable of connecting to the network 110, assessing servers or websites on the network 110, processing data or signals, etc. For example, the terminal device 130 and the terminal device 140 may be desktop computers, laptops, tablets, smart phones, etc. Although only two terminal devices are shown in FIG. 1, it should be appreciated that a different number of terminal devices may connect to the network 110.

In an implementation, the terminal device 130 may be used by a user. The terminal device 130 may include a chatbot client 132 which may provide automated chatting service for the user. In some cases, the chatbot client 132 may interact with the chatbot server 120. For example, the chatbot client 132 may transmit messages input by the user to the chatbot server 120, and receive responses associated with the messages from the chatbot server 120. However, it should be appreciated that, in other cases, instead of interacting with the chatbot server 120, the chatbot client 132 may also locally generate responses to messages input by the user. Herein, "messages" may refer to any input information, e.g., queries from the user, answers of the user to questions from the chatbot, etc.

In an implementation, the terminal device 140 may be used by a psychologist. The terminal device 140 may include a chatbot client 142 which may provide automated chatting service for the psychologist. In some cases, the chatbot client 142 may interact with the chatbot server 120. For example, the chatbot client 142 may transmit messages input by the psychologist to the chatbot server 120, and receive responses associated with the messages from the chatbot server 120. However, it should be appreciated that, in other cases, instead of interacting with the chatbot server 120, the chatbot client 142 may also locally generate responses to messages input by the psychologist.

In some implementations, the chatbot client 132 and the chatbot client 142 may cooperate with each other. For example, a session connection between the user and the psychologist may be established in a chat flow between the user and the chatbot that is maintained by the chatbot client 132 in the terminal device 130. Meanwhile, the session connection may also be presented in a chat flow between the psychologist and the chatbot that is maintained by the chatbot client 142 in the terminal device 140. Herein, "session" may refer to a time-continuous dialog between two chatting participants, and may include messages and responses in the dialog; "session connection" may refer to a connection for carrying a session; and "chat flow" may refer to a chatting procedure including messages and responses from two chatting participants, and may comprise one or more sessions.

The chatbot server 120 may connect to or incorporate a chatbot database 122. The chatbot database 122 may comprise information that can be used by the chatbot server 120 for generating responses.

It should be appreciated that all the network entities shown in FIG. 1 are exemplary, and depending on specific application requirements, any other network entities may be involved in the application scenario 100.

Figure 2:
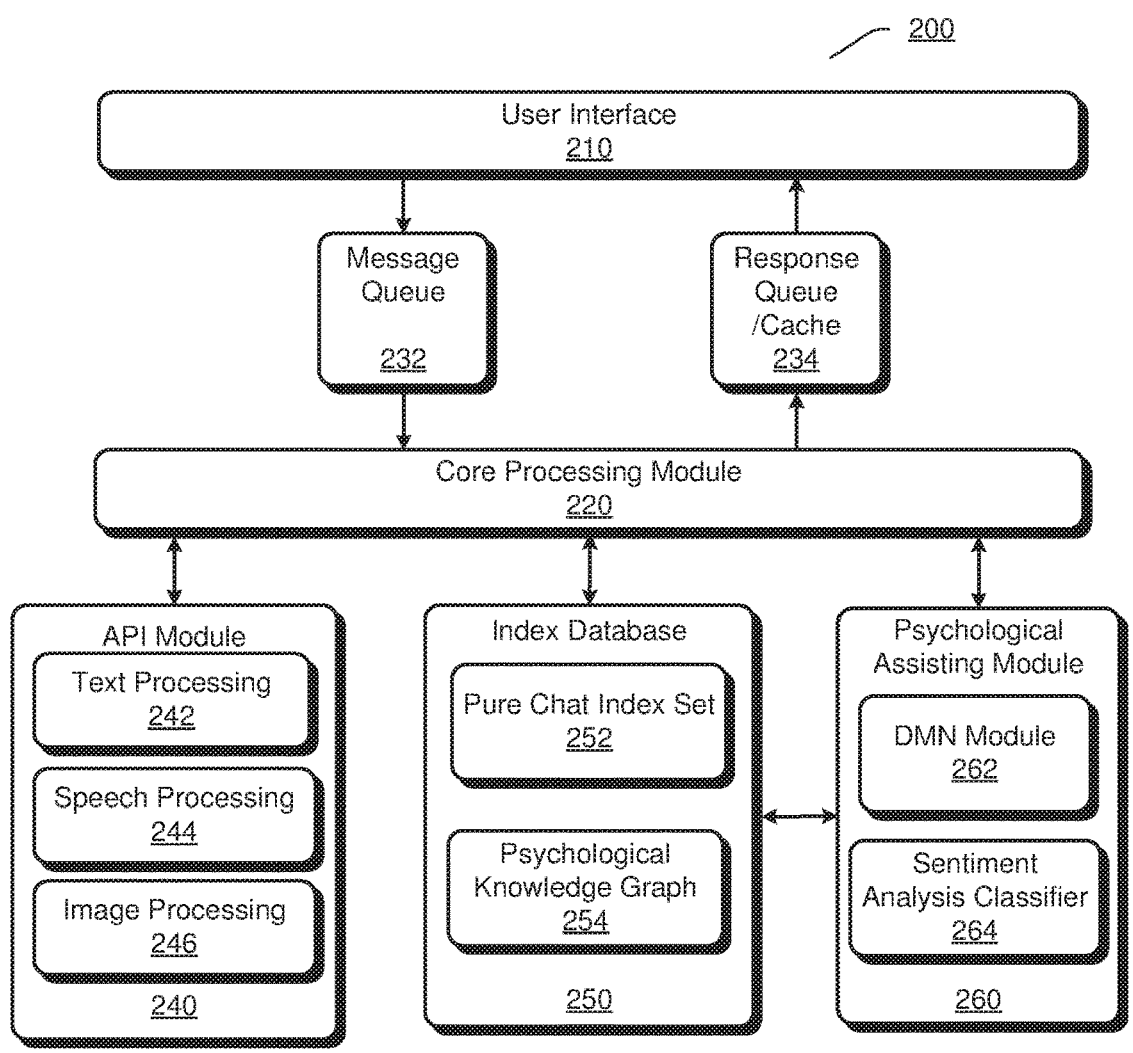
FIG. 2 illustrates an exemplary chatbot system according to an embodiment.

FIG. 2 illustrates an exemplary chatbot system 200 according to an embodiment.

The chatbot system 200 may comprise a UI 210 for presenting a chat window. The chat window may be used by the chatbot for interacting with a user or a psychologist.

The chatbot system 200 may comprise a core processing module 220. The core processing module 220 is configured for, during operation of the chatbot, providing processing capabilities through cooperation with other modules of the chatbot system 200.

The core processing module 220 may obtain messages input by the user or psychologist in the chat window, and store the messages in the message queue 232. The messages may be in various multimedia forms, such as, text, speech, image, video, etc.

The core processing module 220 may process the messages in the message queue 232 in a first-in-first-out manner. The core processing module 220 may invoke processing units in an application program interface (API) module 240 for processing various forms of messages. The API module 240 may comprise a text processing unit 242, a speech processing unit 244, an image processing unit 246, etc.

For a text message, the text processing unit 242 may perform text understanding on the text message, and the core processing module 220 may further determine a text response.

For a speech message, the speech processing unit 244 may perform a speech-to-text conversion on the speech message to obtain text sentences, the text processing unit 242 may perform text understanding on the obtained text sentences, and the core processing module 220 may further determine a text response. If it is determined to provide a response in speech, the speech processing unit 244 may perform a text-to-speech conversion on the text response to generate a corresponding speech response.

For an image message, the image processing unit 246 may perform image recognition on the image message to generate corresponding texts, and the core processing module 220 may further determine a text response. In some cases, the image processing unit 246 may also be used for obtaining an image response based on the text response.

Moreover, although not shown in FIG. 2, the API module 240 may also comprise any other processing units. For example, the API module 240 may comprise a video processing unit for cooperating with the core processing module 220 to process a video message and determine a response.

The core processing module 220 may determine responses through an index database 250. The index database 250 may comprise a plurality of index items that can be retrieved by the core processing module 220 as responses. The index items in the index database 250 may be classified into a pure chat index set 252 and a psychological knowledge edge graph 254. The pure chat index set 252 may comprise index items that are prepared for free chatting between the chatbot and users or psychologists, and may be established with data from, e.g., social networks. The index items in the pure chat index set 252 may or may not be in a form of question-answer (QA) pair. Question-answer pair may also be referred to as message-response pair. The psychological knowledge graph 254 may comprise a number of psychological data pairs in one or more psychological domains. A psychological data pair may be denoted as <Data 1, Data 2>, where a first data "Data 1" and a second data "Data 2" are a pair of psychological data that are relevant to each other.

The chatbot system 200 may comprise a psychological assisting module 260. The psychological assisting module 260 may be used for assisting psychological cure according to the embodiments of the present disclosure. For example, the psychological assisting module 260 may output cure strategies, emotion curves, etc., and the core processing module 220 may take outputs of the psychological assisting module 260 as responses.

The psychological assisting module 260 may comprise a DMN module 262, which is used for performing DMN-based reasoning to generate a cure strategy. The psychological assisting module 260 may comprise a sentiment analysis classifier 264, which is used for performing sentiment analysis on input messages. Moreover, although not shown, the psychological assisting module 260 may further comprise any modules that can be implemented for assisting psychological cure according to the embodiments of the present disclosure.

The responses determined by the core processing module 220 may be provided to a response queue or response cache 234. For example, the response cache 234 may ensure that a sequence of responses can be displayed in a pre-defined time stream. Assuming that, for a message, there are no less than two responses determined by the core processing module 220, then a time-delay setting for the responses may be necessary. For example, if a message input by the player is "Did you eat your breakfast?", two responses may be determined, such as, a first response "Yes, I ate bread" and a second response "How about you? Still feeling hungry?". In this case, through the response cache 234, the chatbot may ensure that the first response is provided to the player immediately. Further, the chatbot may ensure that the second response is provided in a time delay, such as 1 or 2 seconds, so that the second response will be provided to the player 1 or 2 seconds after the first response. As such, the response cache 234 may manage the to-be-sent responses and appropriate timing for each response.

The responses in the response queue or response cache 234 may be further transferred to the UT 210 such that the responses can be displayed to the user in the chat window.

It should be appreciated that all e elements shown in the chatbot system 200 in FIG. 2 are exemplary, and depending on specific application requirements, any shown elements may be omitted and any other elements may be involved in the chatbot system 200.

Figure 3:
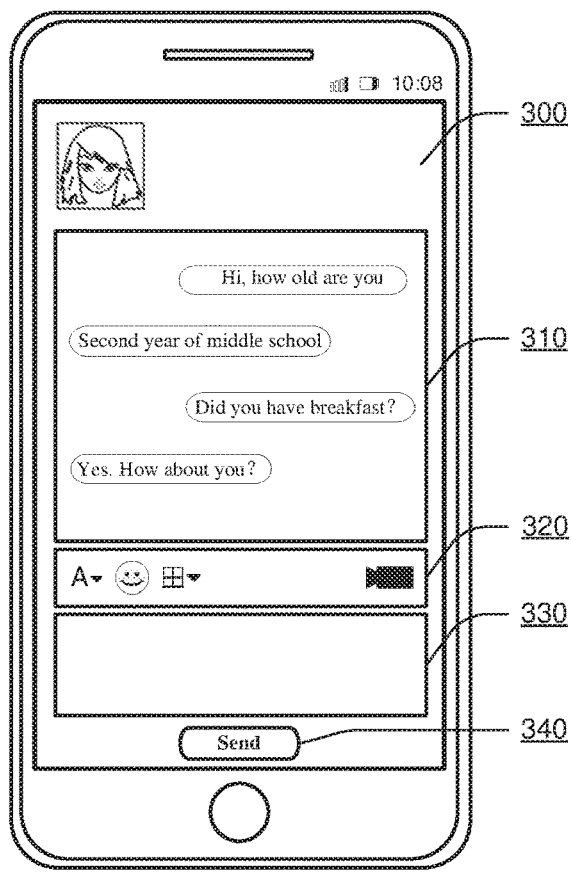
FIG. 3 illustrates an exemplary user interface according to an embodiment.

FIG. 3 illustrates an exemplary user interface 300 according to an embodiment.

The user interface 300 is included in a terminal device, and may comprise a presentation area 310, a control area 320 and an input area 330. The presentation area 310 displays messages and responses in a chat flow. The control area 320 includes a plurality of virtual buttons for the user or psychologist to perform message input settings. For example, the user or psychologist may select to make a voice input, attach image files, select emoji symbols, make a short-cut of the current screen, etc. through the control area 320. The input area 330 is used by the user or psychologist for inputting messages. For example, the user or psychologist may type text through the input area 330. The chat window 300 may further comprise a virtual button 340 for confirming to send input messages. If the user or psychologist touches the virtual button 340, the messages input in the input area 330 may be sent to the presentation area 310.

It should be noted that all the elements and their layout shown in FIG. 3 are exemplary. Depending on specific application requirements, the user interface in FIG. 3 may omit or add any elements, and the layout of the elements in the user interface in FIG. 3 may also be changed in various approaches.

Figure 4:
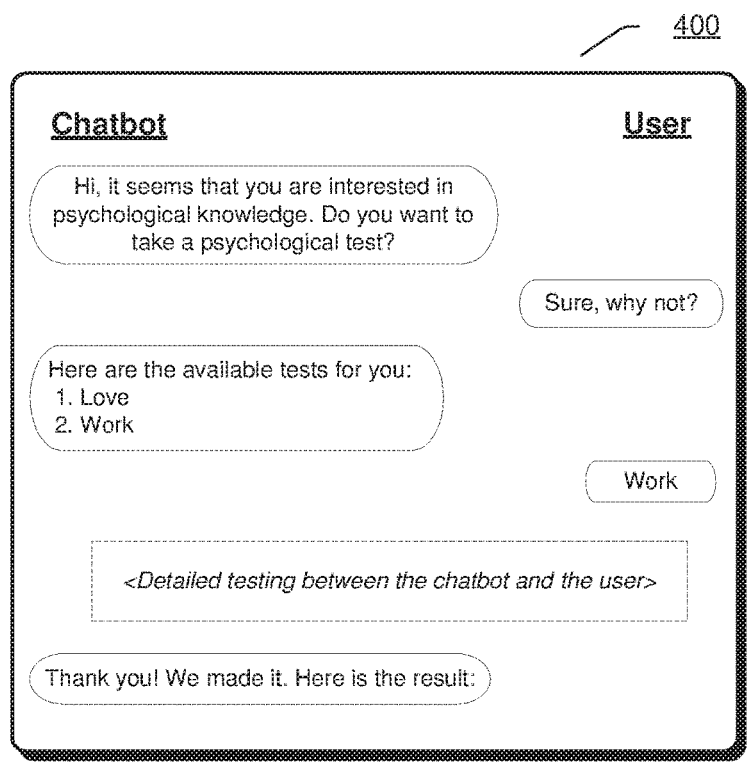
FIG. 4 illustrates an exemplary chat window according to an embodiment.

FIG. 4 illustrates an exemplary chat window 400 between a chatbot and a user according to an embodiment. The chat window 400 shows a procedure of performing an explicit psychological test. The explicit psychological test may also be referred to as a formatted psychological test, and may comprise a plurality of psychological questions and reference answers that are predetermined artificially or automatically. There may be various types of explicit psychological tests that belong to various psychological domains, e.g., "Love", "Work", "Family", "Interpersonal relationship", etc.

An explicit psychological test may be determined to be performed if the user explicitly requires a psychological test by inputting a message, e.g., "I want to take a psychological test". Moreover, an explicit psychological test may also be determined to be performed if the user inputs a message including a positive response, e.g., "Yes", to a question, e.g., "Do you want to take a psychological test?" from the chatbot. An example of the latter is shown in the chat window 400. However, it should be appreciated that the chat flow in the chat window 400 is exemplary, and the embodiments of the present invention are not limited to any detailed expressions or procedures in the chat window 400.

As shown in the chat window 400, when the chatbot asks "Do you want to take a psychological test?", the user inputs a message "Sure, why not?" as a reply. The chatbot may determine, based on the message input by the user, that the user accepts to take a psychological test, and thus an explicit psychological test may be conducted.

The chatbot may provide the user with two options, e.g., "Love" and "Work", that belong to different psychological domains. When the user chooses "Work", the chatbot may begin to conduct an explicit psychological test in a "Work" domain. During the test, the chatbot may send psychological questions to the user, and receive the user's answers. An exemplary psychological question may be "Can you focus on your job in your current working environment?", and an exemplary answer "Sometimes yes" may be received from the user.

The chatbot may score the user's answers based on a scoring algorithm predefined by psychologists or experts in psychological domains, and may provide a result of the psychologist test. In an implementation, the chatbot may compare a user's answer to a psychological question in the psychological test with one or more reference answers predefined for the psychological question, and provide a score for the user's answer accordingly.

Figure 5:
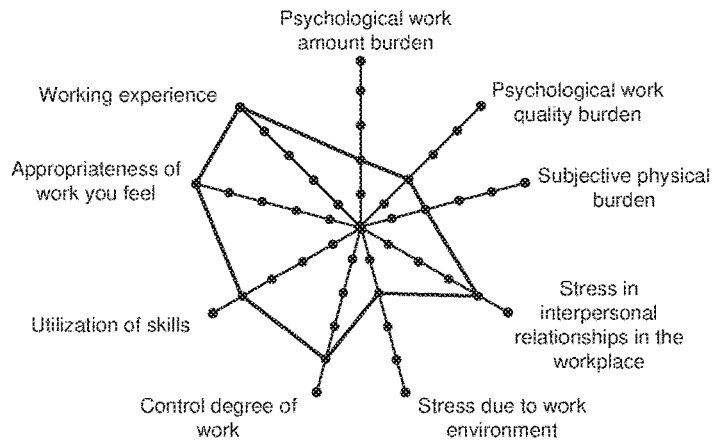
FIG. 5 illustrates an exemplary result of a psychologist test according to an embodiment.
Figure 5:
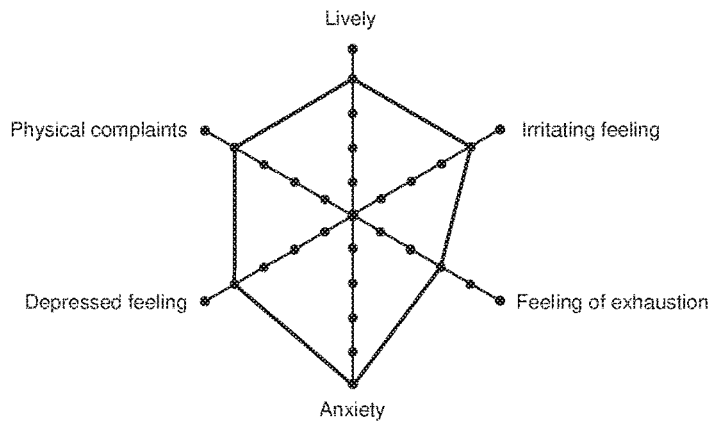
Figure 5:
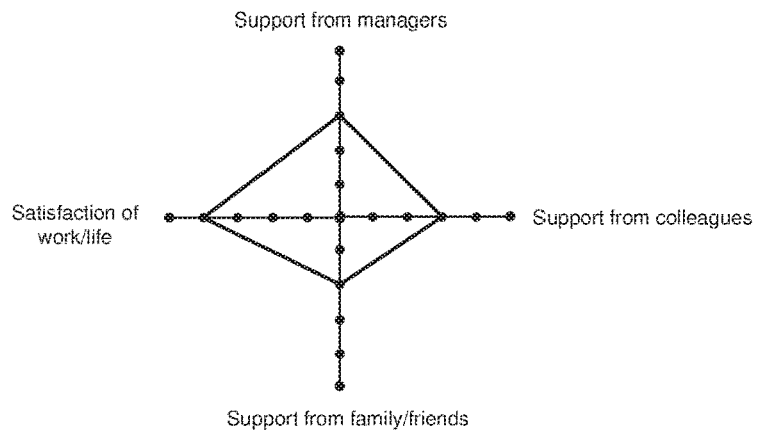

FIG. 5 illustrates an exemplary result 500 of a psychological test according to an embodiment. The psychological test may be in a work domain as performed in FIG. 4 for the user. The result 500 of the psychological test may be presented in the chat window 400, or in any other independent windows shown in a terminal device.

As shown in FIG. 5, the result 500 may comprise three exemplary parts, e.g., "Potential reasons of stress" 510, "Body reactions caused by stress" 520 and "Factors that influence reactions" 530.

In the part of "Potential reasons of stress" 510, there are nine dimensions which are considered as factors causing stress. Each dimension is scaled by five levels. The nine dimensions may comprise, such as, Psychological work amount burden, Psychological work quality burden, Subjective physical burden, Stress in interpersonal relationships in the workplace, Stress due to work environment, Control degree of work, Utilization of skills, Appropriateness of work you feel, and Working Experience. Levels in the nine dimensions obtained by the user may be determined as, e.g., [2, 2, 2, 4, 2, 4, 4, 5, 5] respectively based on the user's answers. A graph formed by connecting lines among the determined levels as shown in FIG. 5 may integrally represent an evaluation on the user in the part of "Potential reasons of stress".

In the part of "Body reactions caused by stress" 520, there are six dimensions for representing body reactions. Each dimension is scaled by five levels. The six dimensions may comprise, such as, Lively, Irritating feeling, Feeling of exhaustion, Anxiety, Depressed feeling and Physical complaints. Levels in the six dimensions obtained by the user may be determined as, e.g., [4, 4, 3, 5, 4, 4] respectively based on the user's answers. A graph formed by connecting lines among the determined levels as shown in FIG. 5 may integrally represent an evaluation on the user in the part of "Body reactions caused by stress".

In the part of "Factors that influence reactions" 530, there are four dimensions for representing factors that may influence reactions. Each dimension is scaled by five levels. The four dimensions may comprise, such as, Support from managers, Support from colleagues, Support from family and/or friends, and Satisfaction of work and/or life. Levels in the four dimensions obtained by the user may be determined as, e.g., [3, 3, 2, 4] respectively based on the user's answers. A graph formed by connecting lines among the determined levels as shown in FIG. 5 may integrally represent an evaluation on the user in the part of "Factors that influence reactions".

If the result 500 is provided to the user, the result 500 may be helpful for the user to intuitively understand his/her psychological condition and to determine whether to ask for a psychological help or cure. On the other hand, the result 500 may also be provided to a psychologist by the chatbot, and the psychologist may consequently determine whether to track the user or determine a cure strategy.

It should be appreciated that the result 500 is not limited to be in the form of graph as shown in FIG. 5, the result 500 may also be presented in tables, literal descriptions, etc. All the elements in the result 500, such as, the three parts, dimensions in each part, levels scaled in each dimension, etc., are exemplary, and depending on specific application requirements, the result of the psychological test may comprise any other equivalents, replacements, or revisions.

Figure 6:
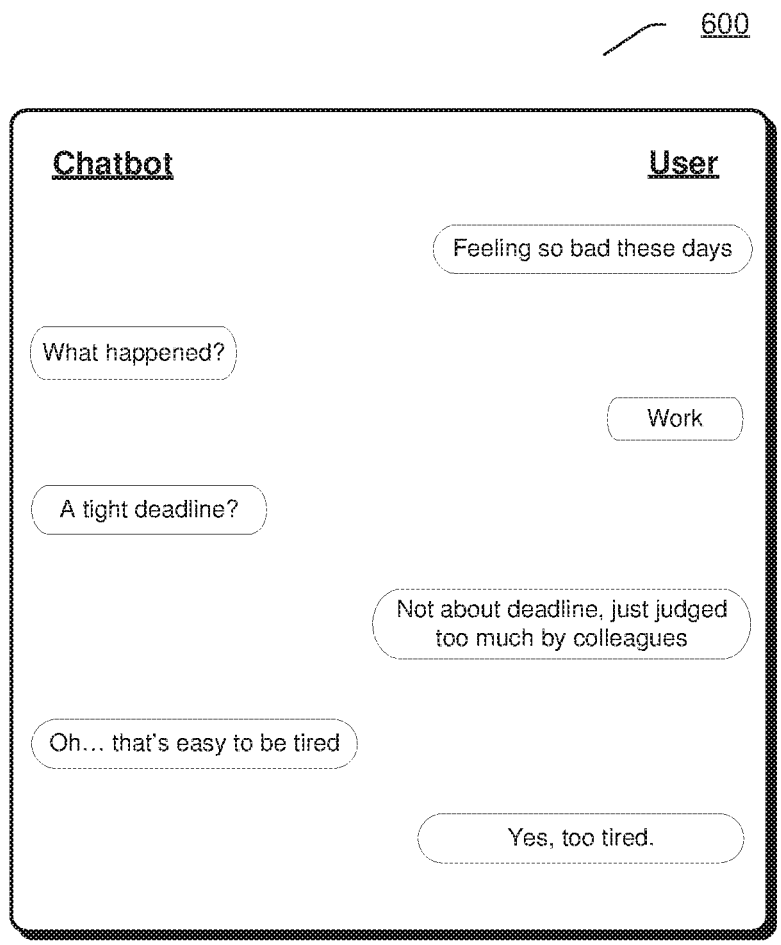
FIG. 6 illustrates an exemplary chat window according to an embodiment.

Moreover, it should be appreciated that the result 500 is from the psychological test in the work domain, and there may be various results for psychological tests in other psychological domains, FIG. 6 illustrates an exemplary chat window 600 between a chatbot and a user according to an embodiment. The chat window 600 shows a procedure of performing an implicit psychological test.

The implicit psychological test may refer to performing a psychological test in an implicit way, such as, sending psychological questions and receiving the user's answers in a session of a chat flow in a way that is not recognizable for the user. The psychological questions in the implicit psychological test may be generated based on messages input by the user in the current session of the chat flow, or based on transformation of psychological questions in a formatted psychological test as mentioned in FIG. 4, where the transformation of psychological questions in the formatted psychological test may intend to express the psychological questions in an implicit way. In some cases, it is important to perform the implicit psychological test, for the purpose of not taking too much time of the user, or avoiding that the user answers in an imaginary or fake way when the user is told to take a psychological test.

As shown in the chat window 600, when the user inputs a message "Feeling so bad these days", the chatbot may determine that the user is in a negative emotion. Thus, the chatbot may further try to perform an implicit psychological test. For example, the chatbot may ask "What happened?" so as to start the implicit psychological test.

When receiving an answer "Work" from the user, the chatbot may further ask a question "A tight deadline?" which is generated in a psychological "Work" domain for determining reasons of the negative emotion of the user.

The user may answer by "Not about deadline, just judged too much by colleagues". Thus, the chatbot may acknowledge that the user has the negative emotion because of interpersonal relationship, e.g., being judged too much by colleagues.

The chatbot may further send a response "Oh . . . that's easy to be tired" so as to confirm body reactions of the user. Then, the user may input a message "Yes, too tired" which confirms that the user feels tired in terms of body reactions.

As discussed above, the chatbot may learn the user's psychological conditions from answers of the user received in the session of the chat flow.

It should be appreciated that the implicit psychological test in the chat window 600 is exemplary, and the embodiments of the present invention are not limited to any detailed expressions or procedures in the chat window 600.

Moreover, although not shown in FIG. 6, it should be appreciated that a result of the implicit psychological test may be generated by the chatbot, which may be in a form as shown in FIG. 5 or in any other forms. Alternatively, the result of the implicit psychological test may also be presented to the user or a psychologist.

According to the embodiments of the present disclosure, besides performing a psychological test as shown in FIG. 4 or FIG. 6, the chatbot may also provide a cure strategy for a user based on a result of the psychological test.

Figure 7:
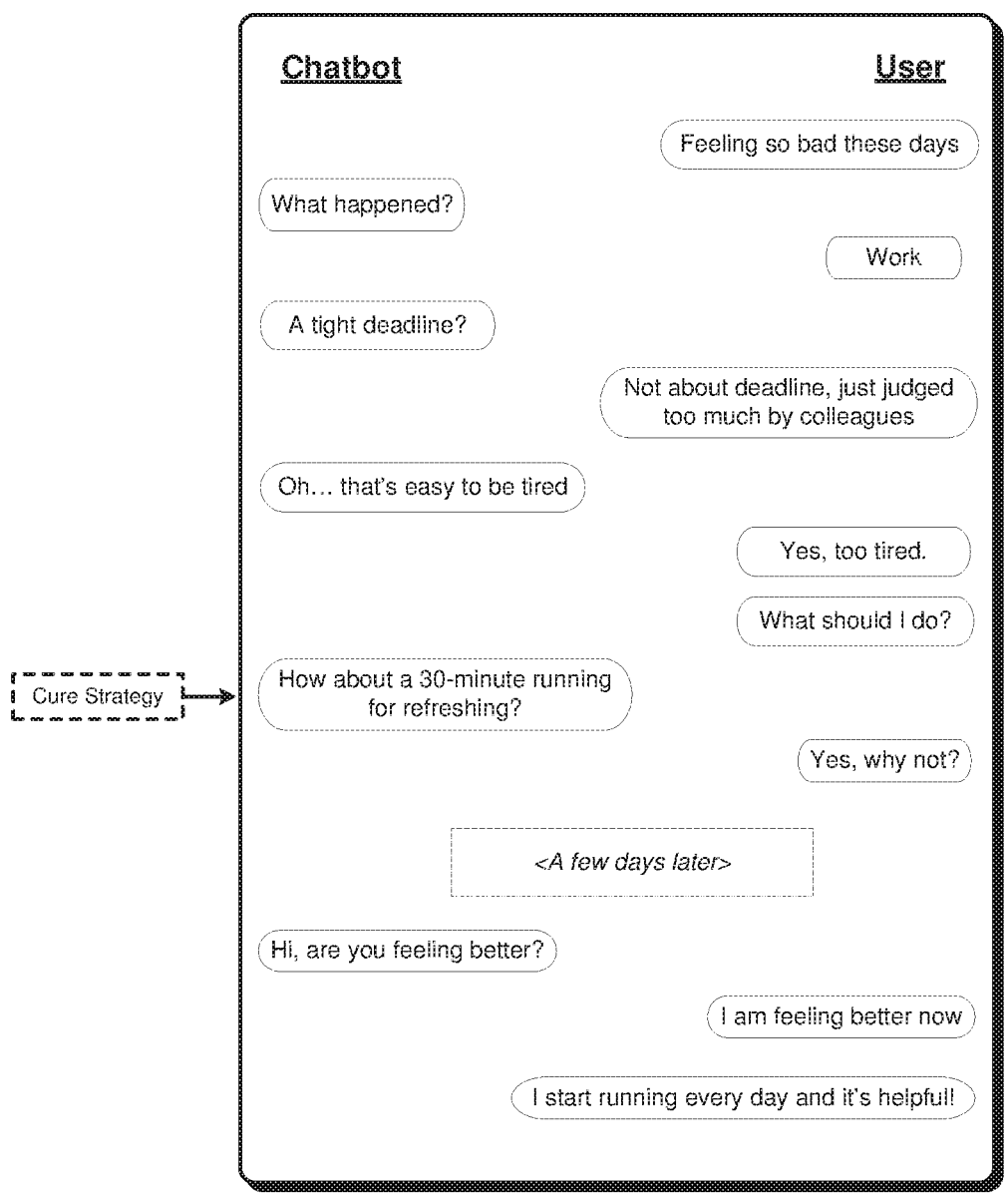
FIG. 7 illustrates an exemplary chat window according to an embodiment.

FIG. 7 illustrates an exemplary chat window 700 between a Chabot and a user according to an embodiment. The chat window 700 shows a procedure of providing a cure strategy by the chatbot to the user, wherein the cure strategy is generated by the chatbot. The chat flow in the chat window 700 may be a continuation of the chat flow shown in the chat window 600 in FIG. 6.

As shown in the chat window 700, after the user inputs a message "Yes, too tired", the user may further ask "What should I do?". The chatbot may determine from the message "What should I do?" that the user requires a cure strategy. Thus, the chatbot may determine, based at least on the current session, a cure strategy "How about a 30-minute running for refreshing?" and provide the cure strategy to the user. The user accepts the cure strategy by answering "Yes, why not?".

After a few days passed, the chatbot may check the effectiveness of the cure strategy previously provided to the user. For example, the chatbot may ask "Hi, are you feeling better?". The user may answer "I am feeling better now. I start running every day and it's helpful". Thus, based on the feedback from the user, the chatbot may know that the cure strategy about "a 30-minute running" for the user is effective.

It should be appreciated that the procedure of providing a cure strategy in the chat window 700 is exemplary, and the embodiments of the present invention are not limited to any detailed expressions or procedures in the chat window 700.

As mentioned above, the chat flow in the chat window 700 is a continuation of the chat flow shown in the chat window 600 in FIG. 6. That is, the cure strategy may be provided in response to implementation of an implicit psychologist test. It should be appreciated that the cure strategy may also be provided in response to implementation of an explicit psychologist test. Thus, the procedure of providing the cure strategy in the chat window 700 may also follow the chat flow in the chat window 400 in FIG. 4.

Figure 8:
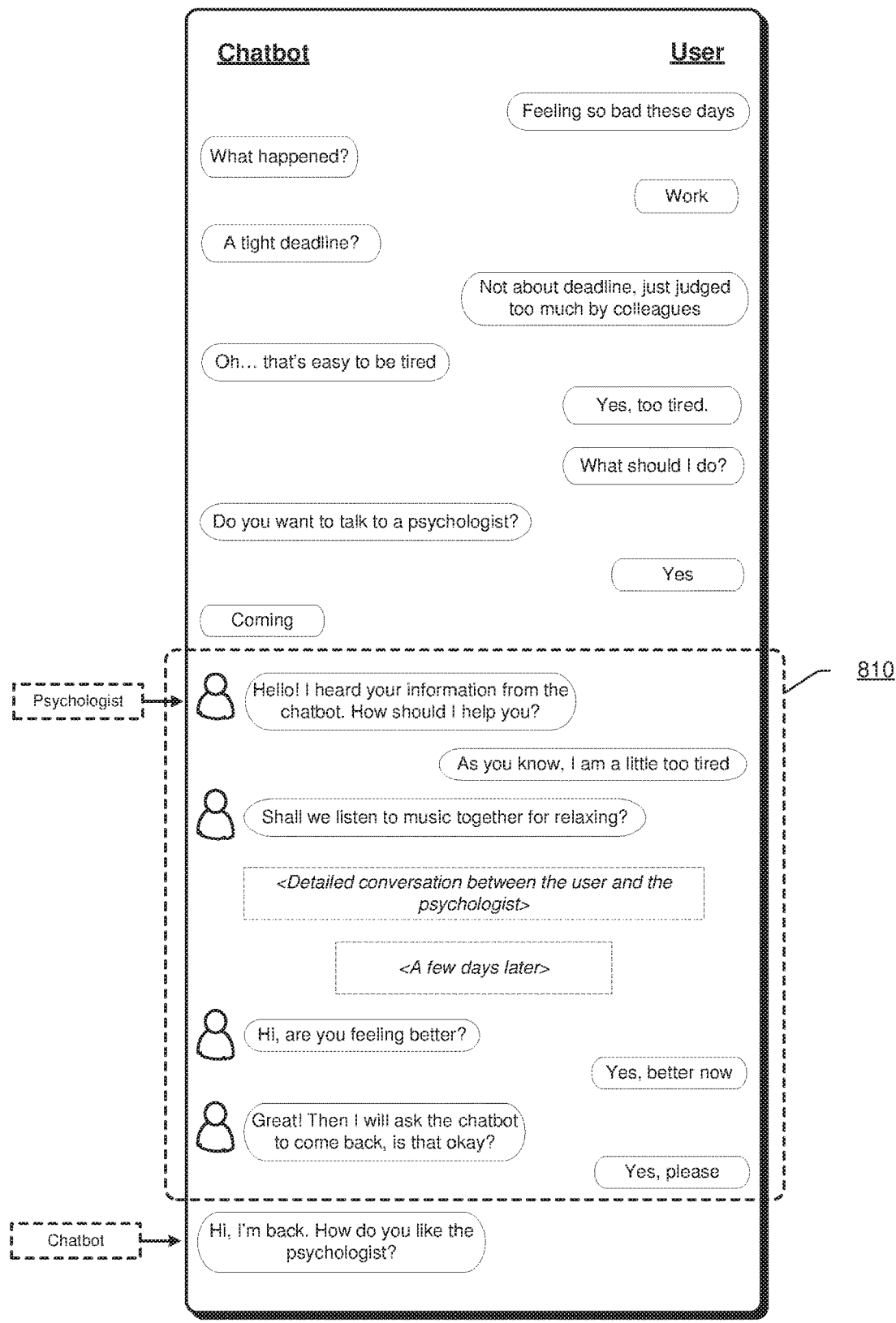
FIG. 8 illustrates an exemplary chat window according to an embodiment.

FIG. 8 illustrates an exemplary chat window 800 between a chatbot and a user according to an embodiment. The chat window 800 shows a procedure of introducing a psychologist to provide a cure strategy. The chat flow in the chat window 800 may be a continuation of the chat flow shown in the chat window 600 in FIG. 6.

As shown in the chat window 800, after the user inputs a message "Yes, too tired", the user may further ask "What should I do?". The chatbot may determine from the message "What should I do?" that the user requires a cure strategy. Thus, the chatbot may decide to introduce a psychologist. The chatbot may ask "Do you want to talk to a psychologist?", and if the user accepts to talk to a psychologist by answering "Yes", the chatbot may establish a session connection between the user and the psychologist in the chat flow.

In some implementations, before establishing the session connection, the chatbot may provide information about the user, such as, psychological conditions, reasons causing the psychological conditions, records of sessions between the chatbot and the user, etc., to the psychologist, and thus the psychologist may determine a corresponding cure strategy. In other implementations, the chatbot may also provide a suggested cure strategy to the psychologist.

As shown in dotted block 810 in FIG. 8, during the session between the user and the psychologist, the psychologist may provide a cure strategy, e.g., "Shall we listen to music together for relaxing?".

After a few days passed, the psychologist may check the effectiveness of the cure strategy previously provided to the user. For example, the psychologist may ask "Hi, are you feeling better?". The user may answer by "Yes, better now". Based on the feedback from the user, the psychologist may know that the cure strategy about listening to music for the user is effective. Then, the psychologist may ask the chatbot back to the chat flow, and the session between the user and the psychologist ends. The chatbot may further chat with the user accordingly.

It should be appreciated that the procedure of introducing the psychologist to provide the cure strategy in the chat window 800 is exemplary, and the embodiments of the present invention are not limited to any detailed expressions or procedures in the chat window 800.

As mentioned above, the chat flow in the chat window 800 is a continuation of the chat flow shown in the chat window 600 in FIG. 6. That is, the psychologist may be introduced in response to implementation of an implicit psychologist test. It should be appreciated that the psychologist may also be introduced in response to implementation of an explicit psychologist test. Thus, the procedure of introducing the psychologist to provide the cure strategy in the chat window 800 may also follow the chat flow in the chat window 400 in FIG. 4.

Figure 9:
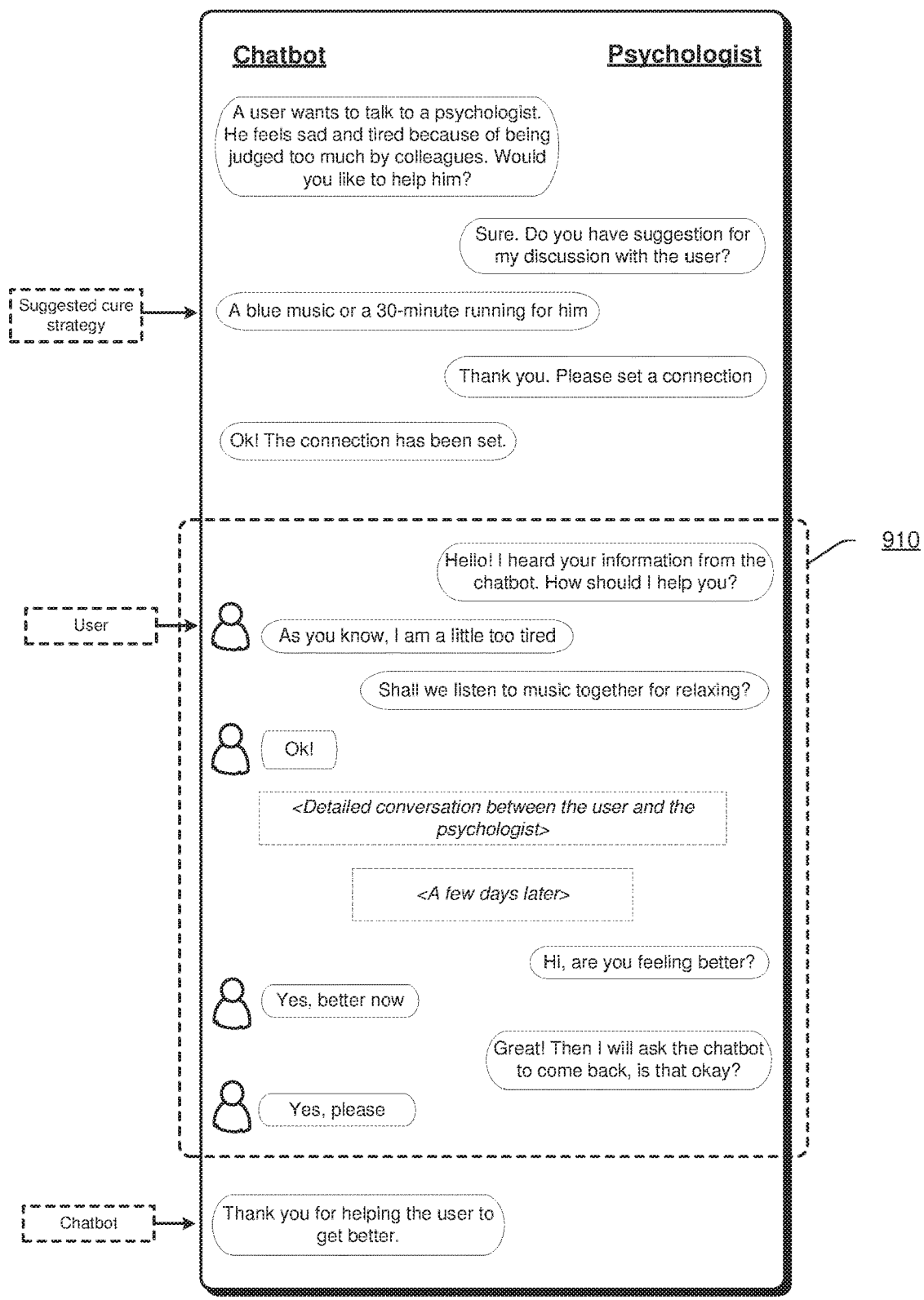
FIG. 9 illustrates an exemplary chat window according to an embodiment.

FIG. 9 illustrates an exemplary chat window 900 between a Chabot and a psychologist according to an embodiment. The chat window 900 shows a procedure of inviting a psychologist to talk to a user. The chat flow in the chat window 900 may correspond to the chat flow shown in the chat window 800 in FIG. 8.

As shown in the chat window 900, the chatbot may send an invitation to the psychologist and provide information about the user, such as, "A user wants to talk to a psychologist. He feels sad and tired because of being judged too much by colleagues. Would you like to help him?". The psychologist may answer by "Sure. Do you have suggestion for my discussion with the user?"

Based on the response from the psychologist, the chatbot may provide the psychologist with a suggested cure strategy "A blue music or a 30-minute running for him". Then, as required by the psychologist, the chatbot may establish a session connection between the psychologist and the user in the chat flow.

As shown in dotted block 910 in FIG. 9, during the session between the psychologist and the user, the psychologist may provide a cure strategy, e.g., "Shall we listen to music together for relaxing?" to the user. The session in dotted block 910 corresponds to the session in dotted block 810 in FIG. 8.

After the session between the psychologist and the user ends, the chatbot may come back to chat with the psychologist accordingly.

It should be appreciated that the procedure of inviting the psychologist to talk to the user in the chat window 900 is exemplary, and the embodiments of the present invention are not limited to any detailed expressions or procedures in the chat window 900. For example, although the chat window 900 includes providing the suggested cure strategy to the psychologist by the chatbot, this part may also be omitted from the procedure in the chat window 900, and thus the psychologist may give a cure strategy to the user based on his/her own judgments.

Moreover, it should be appreciated that the procedure of inviting a psychologist may be performed in response to either an explicit, psychological test or an implicit psychological test. The procedure of inviting a psychologist may even be triggered by an initiative requirement from a user.

Figure 10:
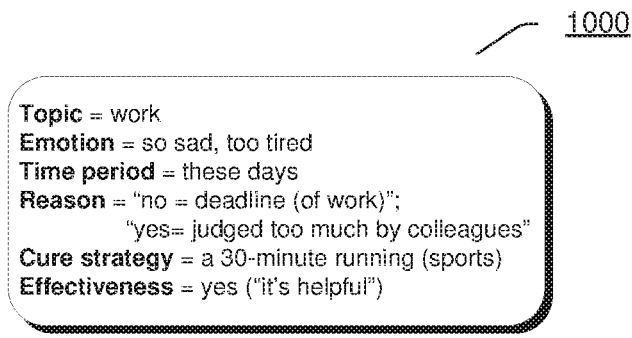
FIG. 10 illustrates an exemplary emotion card according to an embodiment.

FIG. 10 illustrates an exemplary emotion card 1000 according to an embodiment. The emotion card 1000 may refer to a data, collection about a user that contains various psychological condition information of a user. The emotion card 1000 may be established from one or more sessions between the user and the chatbot or between the user and a psychologist. For the user, there may be one or more emotion cards established from one or more sessions of the user.

As shown in FIG. 10, the emotion card 1000 may comprise at least one of topic, emotion, time period, reason, cure strategy and effectiveness. Content in each item of the emotion card 1000 may be extracted from a session. For example, according to the session between the user and the chatbot in FIG. 7, when determining that the feedback from the user is positive, the emotion card 1000 may be generated, based on information extracted from the session between the user and the chatbot, as comprising: Topic=work, which denotes that the topic between the user and the chatbot is about "work"; Emotion=so sad, too tired, which denotes that the emotion of the user is so sad and too tired; Time period=these days, which denotes the negative emotion of the user occurs within these days; Reason="no=deadline (of work)" and "yes=judged too much by colleagues", which denotes that the reason of the emotion is not a deadline of work, but is being judged too much by colleagues; Cure strategy=a 30-minute running (sports), which denotes that a cure strategy relating to sports, e.g., 30-minute running, was provided to the user; and Effectiveness=yes ("it's helpful"), which denotes that the effectiveness of the cure strategy is determined as positive based on a feedback "it's helpful" from the user.

It should be appreciated that, depending on specific application requirements, the emotion card 1000 may further comprise any items other than the ones listed in FIG. 10. Moreover, the emotion card 1000 is not limited to the card format as shown in FIG. 10, but can also be represented in a format of graph, table, etc.

Figure 11:
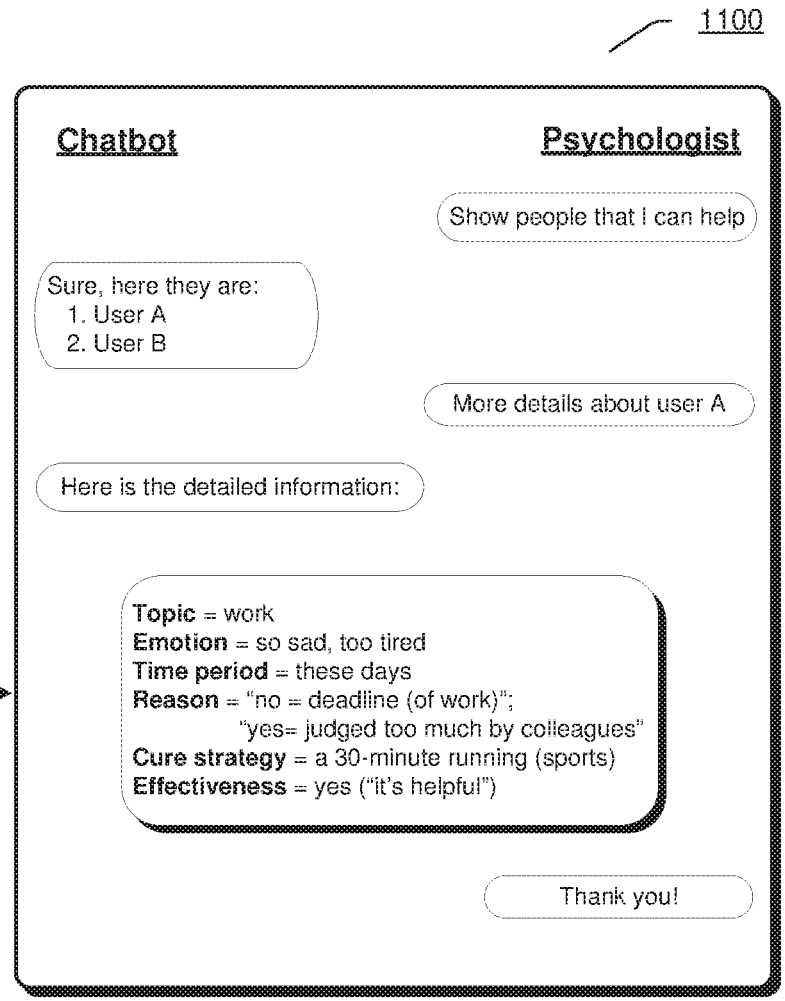
FIG. 11 illustrates an exemplary chat window according to an embodiment.

In an implementation, an emotion card may be provided to a psychologist to help the psychologist to learn user information of a user. FIG. 11 illustrates an exemplary chat window 1100 between a chatbot and a psychologist according to an embodiment. The chat window 1100 shows a procedure of providing an emotion card to the psychologist by the chatbot. As shown in the chat window 1100, the psychologist may request "Show people that I can help". The chatbot may respond by providing a list of users, e.g., User A and User B. When the psychologist inputs a message "More details about User A", the chatbot may provide an emotion card, e.g., the emotion card 1000 in FIG. 10, to the psychologist.

In an implementation, such as, in the chat flow 900 in FIG. 9, an emotion card may be used as a part of the information about the user that is provided to the psychologist when inviting the psychologist.

In an implementation, an emotion card may be provided to a user such that the user may learn his/her own psychological conditions or psychological cure processes.

In an implementation, an emotion card may be used by the chatbot to determine a cure strategy for a user.

As mentioned above, the embodiments of the present disclosure propose a sentiment analysis classifier. The sentiment analysis classifier may classify emotion of text, voice, image and video into a respective category. In an implementation, the sentiment analysis classifier may be of 8 dimensions and may discriminate 8 categories of emotion, including happy, angry, fearful, contemptuous, sad, surprise, disgusted and neutral. It should be appreciated that although the following discussion is related to the sentiment analysis classifier with 8 categories of emotion, the embodiments of the present disclosure are not limited to 8 categories of emotion. Instead, sentiment analysis classifiers with any other number of emotion categories may be obtained under the concept of the present disclosure.

An exemplary sentence with the emotion "happy" may be "I'm so glad to hear that!". An exemplary sentence with the emotion "angry" may be "How dare you ignore that!". An exemplary sentence with the emotion "fearful" may be "It's a terrible accident". An exemplary sentence with the emotion "contemptuous" may be "only a computer cannot be that swagger". An exemplary sentence with the emotion "sad" may be "I don't like it and want to cry". An exemplary sentence with the emotion "surprise" may be "What? Really?". An exemplary sentence with the emotion "disgusted" may be "He is more stupid than I expected". An exemplary sentence with the emotion "neutral" may be "Tomorrow's schedule is determined".

Figure 12:
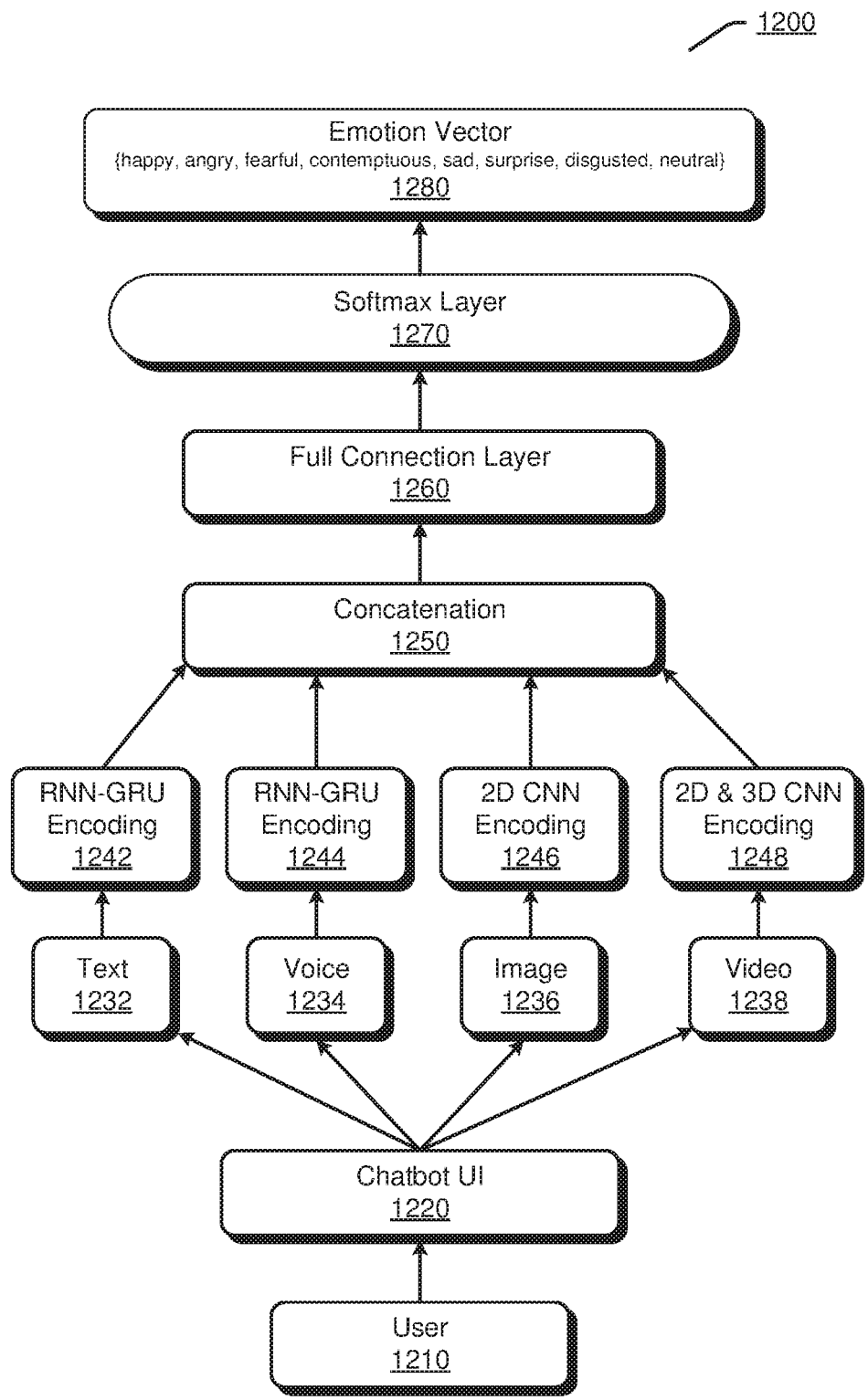
FIG. 12 illustrates an exemplary sentiment analysis model according to an embodiment.

FIG. 12 illustrates an exemplary sentiment analysis model 1200 according to an embodiment. The sentiment analysis model 1200 may project user inputs into dense vectors and further classify the user inputs into respective emotion category in a vector space. The sentiment analysis model 1200 may be implemented by a sentiment analysis classifier according to the embodiments of the present disclosure.

A user 1210 may input a message through a UI 1220 of a chatbot. The user's input may be at least one of a text input 1232, a voice input 1234, an image input 1236 and a video input 1238. The text input 1232 and the image input 1236 may be captured in an input area of the UI 1220, and the voice input 1234 and the video input 1238 may be captured by a microphone or a camera in a terminal device.

In an implementation, a recurrent neural network (RNN)-gated recurrent unit (GRU) encoding 1242 may be performed on the text input 1232. The RNN-GRU encoding 1242 may be used for generating a dense vector representation for the text input 1232. For example, the RNN-GRU encoding 1242 may comprise a one-hot word embedding layer and one or more RNN-GRU layers. A Word2vec technique may be adopted for word embedding in the one-hot word embedding layer. The GRU in the RNN-GRU layers may be unidirectional, e.g., from left to right or from right to left, or may be bidirectional, e.g., both from left to right and from right to left.

Internal mechanism of the GRU may be defined by the following equations:

$$z_t = \sigma(W^{(z)}x_t + U^{(z)}h_{t-1} + b^{(z)}) \quad \text{Equation (1)}$$

$$r_t = \sigma(W^{(r)}x_t + U^{(r)}h_{t-1} + b^{(r)}) \quad \text{Equation (2)}$$

$$\tilde{h}_t = \tanh(Wx_t + r_t \circ Uh_{t-1} + b^{(h)}) \quad \text{Equation (3)}$$

$$h_t = z_t \circ h_{t-1} + (1 - z_t) \circ \tilde{h}_t \quad \text{Equation (4)}$$

where ° is an element-wise product, $W^{(z)}$, $W^{(r)}$, W, $U^{(z)}$, U are weight matrixes, $W^{(z)}$, $W^{(r)}$, $W \in R^{n_H \times n_I}$, and $U^{(z)}$, $U^{(r)}$, $U \in R^{n_H \times n_H}$. Here, $n_H$ denotes a dimension of hidden layer, and $n_I$ denotes a dimension of input layer. The above equations may also be abbreviated as:

$$h_t = GRU(x_t, h_{t-1}) \quad \text{Equation (5)}$$

Through the RNN-GRU encoding 1242 as discussed above, a dense vector representation for the text input 1232 may be obtained.

Figure 13:
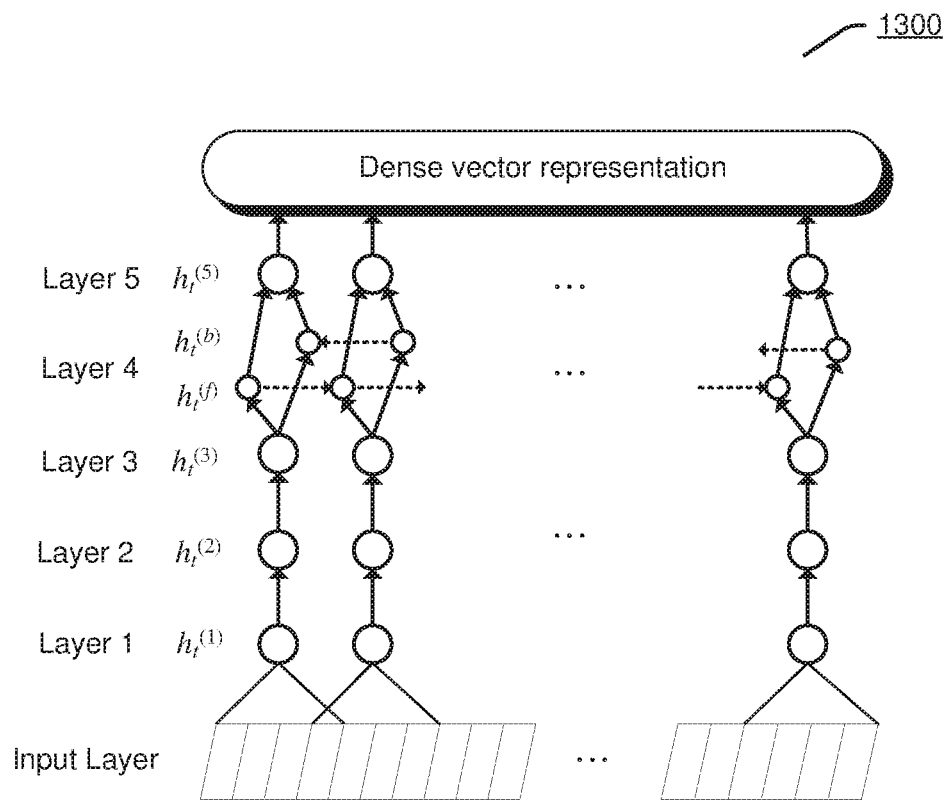
FIG. 13 illustrates an exemplary process for voice encoding according to an embodiment.

In an implementation, a RNN-GRU encoding 1244 may be performed on the voice input 1234. The RNN-GRU encoding 1244 may be used for generating a dense vector representation for the voice input 1234. FIG. 13 illustrates an exemplary process 1300 for voice encoding according to an embodiment. The process 1300 is an example of the RNN-GRU encoding 1244. The process 1300 may project an input voice segments into a dense vector representation.

A voice segment $x^{(i)}$ may be inputted in an Input Layer. The voice segment $x^{(i)}$ may be a time-series with a length of $T^{(i)}$, and each slice is a vector of audio features, denoted as $x_t^{(i)}$, where $t = 1, 2, \ldots, T^{(i)}$. Spectrograms may be used as input features.

As shown in FIG. 13, there are 5 layers of hidden units, denoted as Layer 1 to Layer 5. For an input sequence x, hidden units in Layer l are denoted as $h^{(l)}$, with a special case that $h^{(0)}$ may stand for the input sequence.

Layer 1, Layer 2 and Layer 3 are not recurrent layers. For Layer 1, at each time t, an output depends on a spectrogram frame $x_t$ along with a context of S frames on each side. Empirically, the value of S may be selected from {3, 5, 7, 9} that minimum an error rate of a valuation set. Layer 2 and Layer 3 operate on independent data for each time step. Thus, for each time t, the first 3 layers may be computed as:

$$h_t^l = g(W^{(l)}h_t^{(l-1)} + b^{(l)}) \quad \text{Equation (6)}$$

In Equation (6), a clipped Rectified-Linear activation function g(z) is used, and $W^{(l)}$ and $b^{(l)}$ are weight matrix and bias parameter for Layer l respectively. The function g(z) may be denoted as $g(z) = \min\{\max\{\alpha, z\}, \beta\}$, where α and β are hyper-parameters, and can be adjusted empirically.

Layer 4 is a bi-directional recurrent layer. This layer includes two sets of hidden units, one set for forward left-to-right recurrence $h^{(f)}$, and another set for backward right-to-left recurrence $h^{(b)}$. Internal mechanism of the GRU may follow the above Equations (1) to (5). Thus, $h^{(f)}$ and $h^{(b)}$ may be expressed by:

$$h_t^{(f)} = GRU(h_t^{(3)}, h_{t-1}^{(f)}) \quad \text{Equation (7)}$$

$$h_t^{(b)} = GRU(h_t^{(3)}, h_{t-1}^{(b)}) \quad \text{Equation (8)}$$

Layer 5 is a non-recurrent layer, which takes a concatenation of the forward units and the backward units in Layer 4 as inputs, and may be computed as:

$$h_t^5 = g(W^{(5)}h_t^{(4)} + b^{(5)}) \quad \text{Equation (9)}$$

where $h_t^{(4)}$ is the concatenation of $h_t^{(f)}$ and $h_t^{(b)}$.

Finally, a dense vector representation may be generated from outputs of layer 5.

Through the RNN-GRU encoding 1244 as discussed above, a dense vector representation for the voice input 1234 may be obtained.

In an implementation, a 2D convolutional neutral network (CNN) encoding 1246 may be performed on the image input 1236. The 2D CNN encoding 1246 may be used for generating a dense vector representation for the image input 1236.

Figure 14:
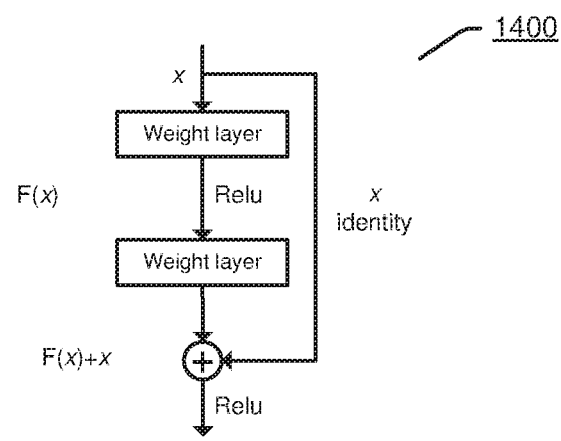
FIG. 14 illustrates an exemplary residual learning block for image encoding according to an embodiment.

Various techniques may be adopted for the 2D CNN encoding 1246. For example, a residual network (ResNet) may be adopted in the 2D CNN encoding 1246. The ResNet may comprise a plurality of residual learning blocks. FIG. 14 illustrates an exemplary residual learning block 1400 for image encoding according to an embodiment. Formally, as for an input x, a desired underlying mapping may be denoted as H(x), and stacked nonlinear layers may fit another mapping of F(x):=H(x)−x. An original mapping may be recast into F(x)+x. It is hypothesized that it is easier to optimize residual mapping than to optimize original unreferenced mapping. To the extreme, if an identity mapping were optimal, it would be easier to push a residual to zero than to fit the identity mapping by a stack of nonlinear layers. The non-linear active function is a rectified linear unit (relu), which may be defined as: Relu(x)=max(0, x).

Figure 15:
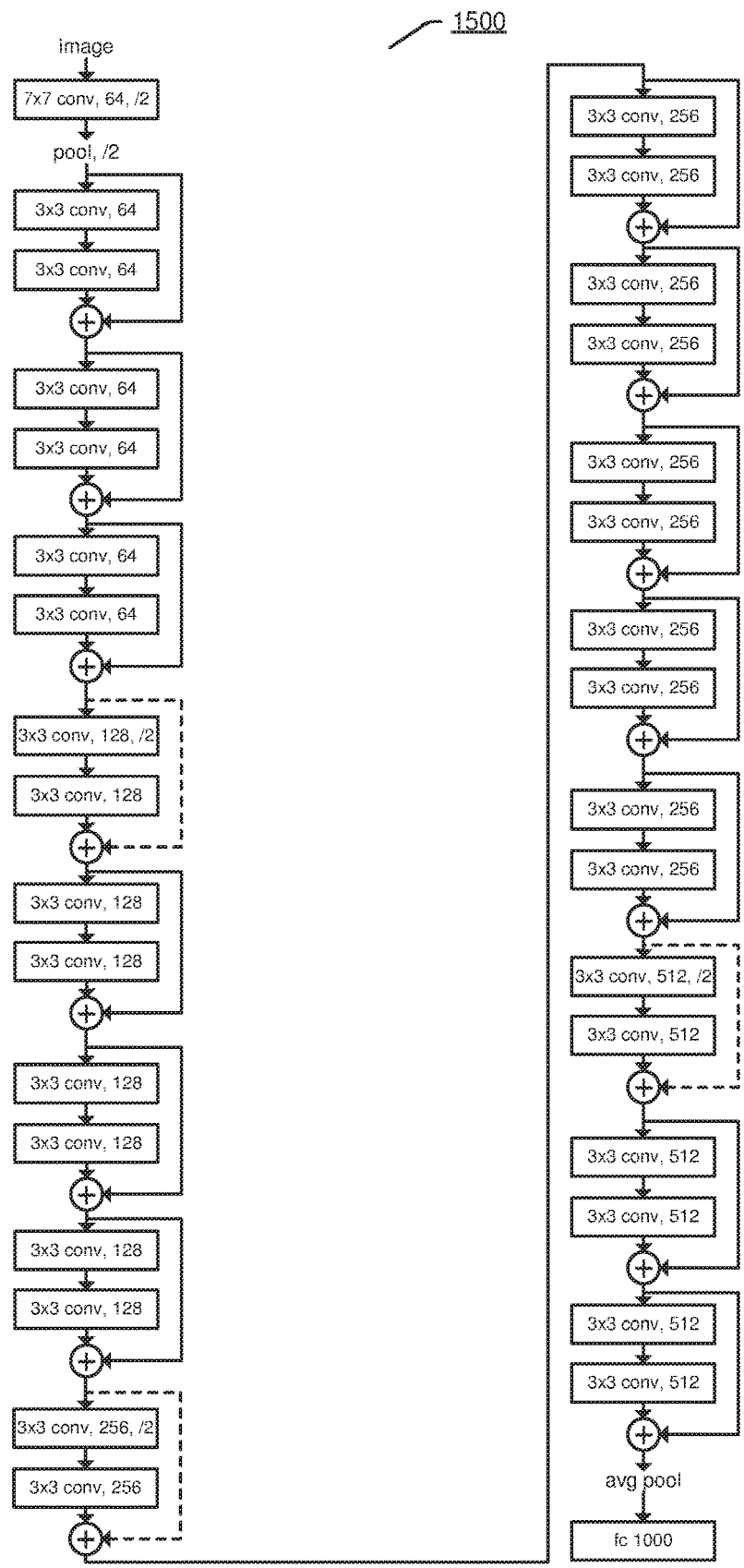
FIG. 15 illustrates an exemplary residual network for image encoding according to an embodiment.

Based on the residual learning block shown in FIG. 14, a residual network may be established. FIG. 15 illustrates an exemplary residual network 1500 for image encoding according to an embodiment. The residual network 1500 has 34 layers, which may provide a relative good accuracy and fast training/testing.

In FIG. 15, for example, "3*3 conv, 64" denotes that there are 64 filters, and each filter has a convolutional kernel or function and is in a scale of 3*3 pixels. "/2" denotes a double stride. "pool" denotes a pooling operation, and "avg pool" denotes an average pooling operation. "fc 1000" denotes a full-connected layer with 1000 output symbols.

Instead of performing "fc 1000", the embodiments of the present disclosure may use an output of the average pooling operation as a dense vector representation for an image input.

It should be appreciated that the ResNet is an exemplary technique that can be adopted in the 2D CNN encoding 1246, and any other techniques may be adopted in the 2D CNN encoding 1246, such as, AlexNet, GoogLeNet, VGG-Net, etc.

Through the 2D CNN encoding 1246 as discussed above, a dense vector representation for the image input 1236 may be obtained.

In an implementation, a 2D and 3D CNN encoding 1248 may be performed on the video input 1238. The 2D and 3D CNN encoding 1248 may be used for generating a dense vector representation for the video input 1238.

Figure 16:
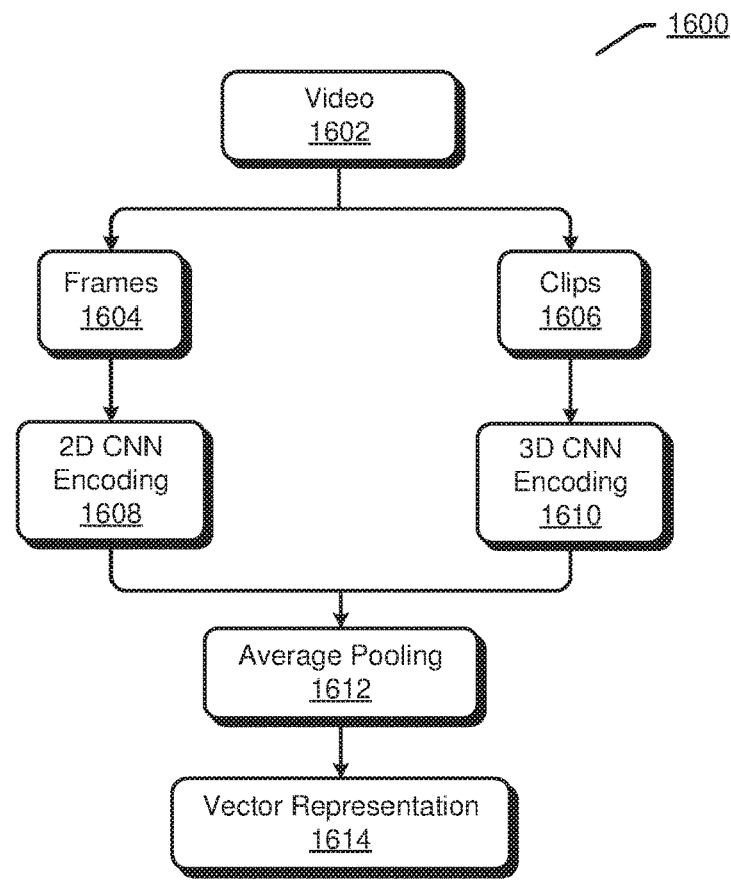
FIG. 16 illustrates an exemplary process for video encoding according to an embodiment.

FIG. 16 illustrates an exemplary process 1600 for video encoding according to an embodiment. The process 1600 may be based on both 2D CNN encoding and 3D CNN encoding.

As shown in FIG. 16, a video input 1602 may be processed in terms of both frame and clip. As for frames 1604 of the video input 1602, a 2D CNN encoding 1608 may be performed. The 2D CNN encoding 1608 may adopt various techniques, e.g., ResNet, AlexNet, GoogLeNet, VGG-Net, etc. As for clips 1606 of the video input 1602, a 3D CNN encoding 1610 may be performed. The 3D CNN encoding 1610 may adopt various techniques, e.g., encoding by convolutional 3D filters, etc. An average pooling operation 1612 may be performed on a combination of an output of the 2D CNN encoding 1608 and an output of the 3D CNN encoding 1610, so as to obtain a dense vector representation 1614 for the video input 1602.

It should be appreciated that the process 1600 in FIG. 16 is an exemplary implementation of the 2D and 3D CNN encoding 1248, and the 2D and 3D CNN encoding 1248 is not limited to any details in the process 1600.

Through the 2D and 3D CNN encoding 1248 as discussed above, a dense vector representation for the video input 1238 may be obtained.

According to the sentiment analysis model 1200 in FIG. 12, a concatenation operation 1250 may be performed on outputs of the RNN-GRU encoding 1242, the RNN-GRU encoding 1244, the 2D CNN encoding 1246, and the 2D and 3D CNN encoding 1248. Through the concatenation operation 1250, a concatenated vector may be obtained.

At a full connection layer 1260, a full connection operation may be performed on the concatenated vector, e.g., multiplying the concatenated vector with a full connection matrix, such that a full connection vector which has a target dimension may be obtained.

A Softmax layer 1270 may map the full connection vector to an emotion vector 1280. The emotion vector 1280 may have 8 dimensions, and each element in the emotion vector 1280 is a probability of a corresponding emotion category. An emotion having the highest probability among the 8 categories of emotion may be selected as the emotion or major emotion of a message input by the user 1210.

The sentiment analysis model 1200 in FIG. 12 is a joint learning model which can project text, voice, image or video inputs into dense vectors and further classify the inputs into respective emotion category in a vector space.

For training the sentiment analysis model 1200, a large scale training data may be prepared. For example, the training data may be obtained from movies with subtitles. Subtitles and images in the movies may be annotated manually by 8-dimension sentiment analysis labels. The labeled subtitles may form training data for text encoding. The labeled subtitles may also be used for forming training data for voice encoding through a conversion between text and voice. The labeled images may form training data for image encoding. The labeled images may also be used for forming training data for video encoding. During training, firstly, the text encoding, the voice encoding, the image encoding and the video encoding may be trained separately. Then, based on the trained text, voice, image and video encoding, the full connection layer 1260 and the Softmax layer 1270 may be further trained.

It should be appreciated that, although the sentiment analysis model 1200 is shown as being capable of processing four types of inputs, including text, voice, image and video inputs, the sentiment analysis model 1200 may also be configured as only processing one, two or three types of inputs. For example, if only text information is available during training and testing, then the sentiment analysis model 1200 may be simplified as a simple "text sentiment analysis model".

Through the sentiment analysis model discussed above, a user's time sensitive emotions may be detected, and an emotion curve may be generated for the user, wherein the emotion curve may be formed from emotion states of the user within a time period. Herein, "emotion state" may also correspond to psychological condition.

Figure 17:
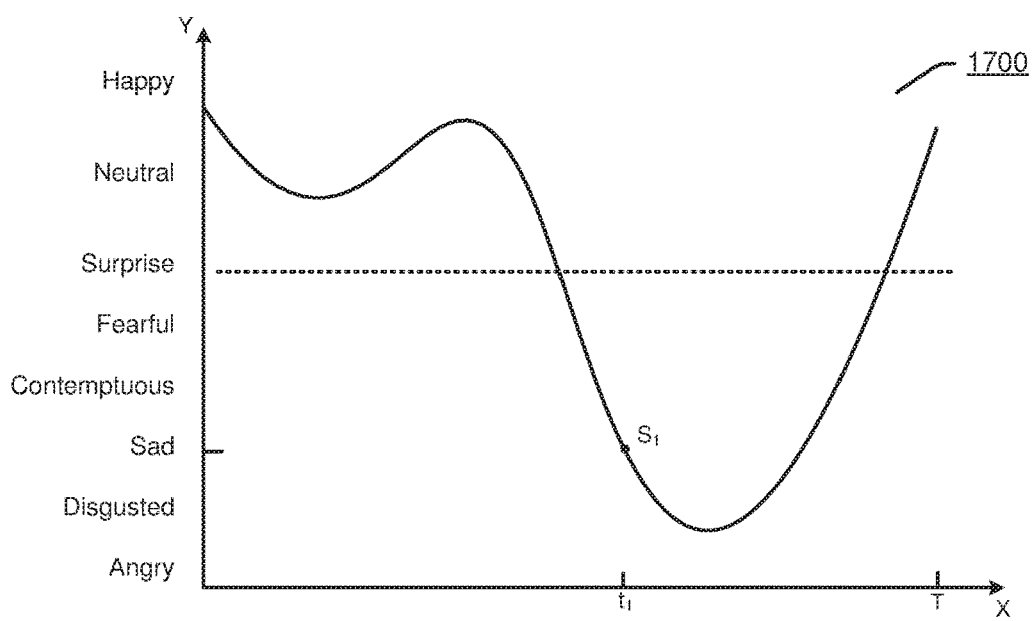
FIG. 17 illustrates an exemplary emotion curve according to an embodiment.

FIG. 17 illustrates an exemplary emotion curve 1700 according to an embodiment. The emotion curve 1700 may indicate emotion states of a user within a time period T. The time period T may be, such as, a week, two weeks, a month, etc. Although the emotion states are shown in a form of curve, it should be appreciated that the emotion curve 1700 is actually formed by a plenty of discrete points, each point corresponding to an emotion determined at a moment.

The X axis in FIG. 17 is a time axis. The minimum time unit in the X axis may be customized, e.g., each message input by the user, each session including a plurality of messages, a certain number of sessions, etc.

The Y axis in FIG. 17 is an emotion state axis. In an implementation, an emotion at each scale in the Y axis and distributions of the scales in the Y axis may be determined through, such as, a Principal Component Analysis (PCA) technique.

Taking a point $S_1$ in the emotion curve 1700 as an example, the point $S_1$ may indicate that the user's emotion is "sad" at the time $t_1$. The emotion of the point $S_1$ may be determined based on, such as, a message input by the user at the time a session ends at the time $t_1$, a group of sessions ends at the time $t_1$, etc. The sentiment analysis model may be used for determining the emotion "sad" of the point $S_1$ based on the message input by the user, the session, the group of sessions, etc.

The dotted line in FIG. 17 is drawn empirically, which may be used for discriminating negative emotions. For example, the part of the emotion curve 1700 that is below the dotted line may be deemed as corresponding to negative emotions. The negative emotions may comprise, such as, angry, disgusted, sad, contemptuous, fearful, or even surprise.

Figure 18:
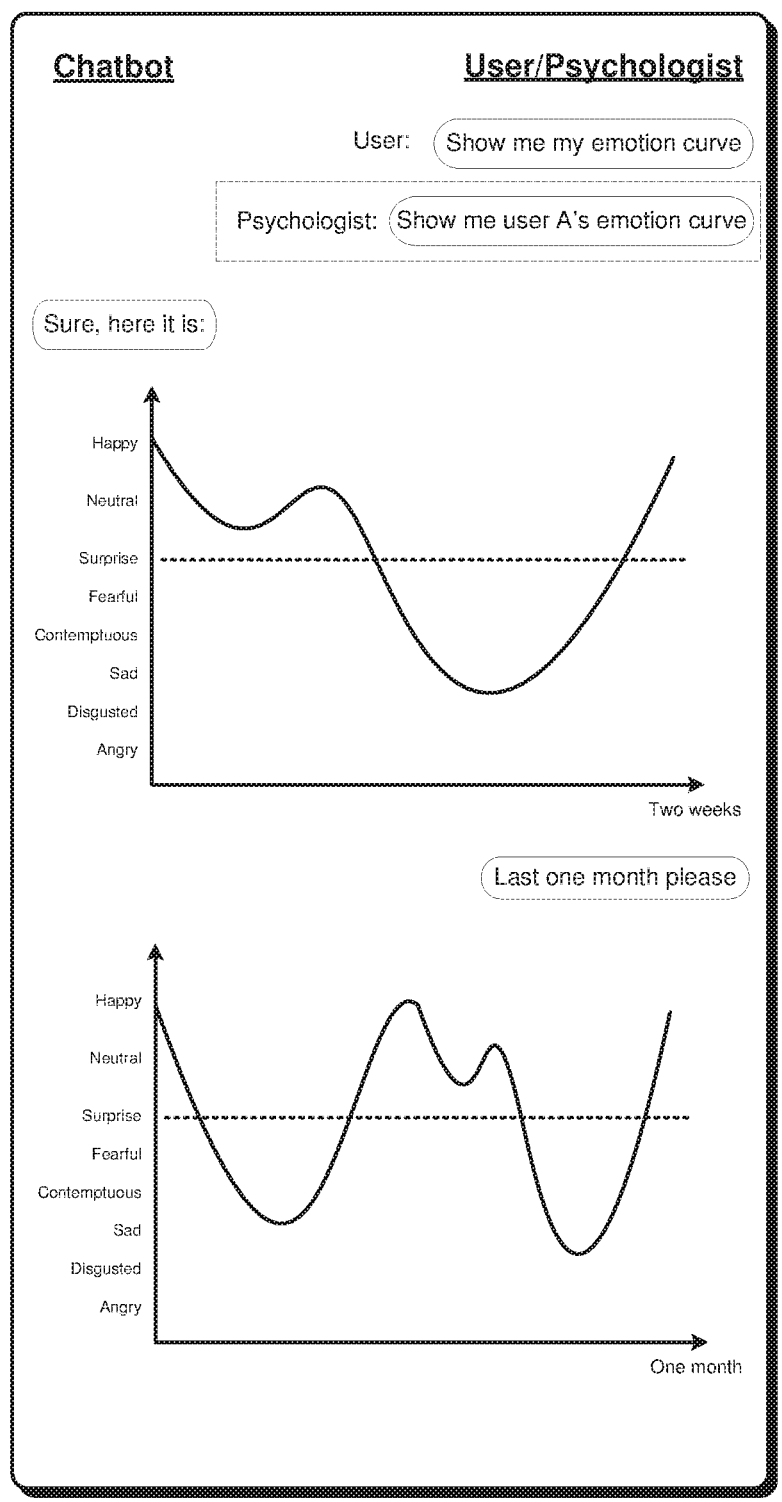
FIG. 18 illustrates an exemplary chat window according to an embodiment.

According to the embodiments of the present disclosure, an emotion curve may be presented to a user or a psychologist by the chatbot. FIG. 18 illustrates an exemplary chat window 1800 between the chatbot and a user or between the chatbot and a psychologist according to an embodiment.

In the case that the chat window 1800 is between the chatbot and the user, when the user requests "Show me my emotion curve", the chatbot may provide an emotion curve of the user determined for last two weeks. When the user desires to see an emotion curve of the last one month, the chatbot may provide the emotion curve determined for the last one month.

In the same way, if the chat window 1800 is between the chatbot and the psychologist, in response to a request from the psychologist, the chatbot may also provide a corresponding emotion curve.

According to the embodiments of the present disclosure, a psychological knowledge graph may be established. The psychological knowledge graph may be specific to one psychological domain, or directs to two or more psychological domains. The psychological knowledge graph may be used by the chatbot for answering user's questions, performing psychological tests, determining cure strategies for users, etc.

Figure 19:
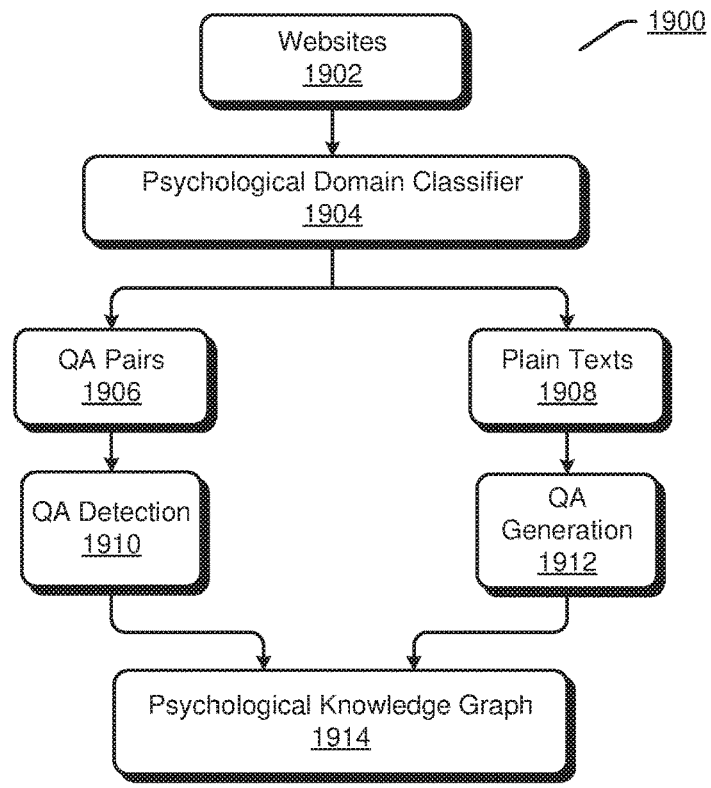
FIG. 19 illustrates an exemplary process for establishing a psychological knowledge graph according to an embodiment.

FIG. 19 illustrates an exemplary process 1900 for establishing a psychological knowledge graph according to an embodiment. The process 1900 may generate psychological data pairs from plain texts or QA pairs in a psychological domain on at least one website through data mining. In some implementations, a generated psychological data pair <Data 1, Data 2> in the process 1900 may also be represented in a QA format, e.g., <Question,Answer>.

There are a number of websites 1902 on the network that provide various contents. A psychological domain classifier 1904 may be used for classifying contents on the websites 1902 into respective psychological domains, e.g., "Love", "Work", "Family", "Interpersonal relationship", etc. The contents in psychological domains may comprise psychological articles, psychological news or reports, psychological consultations, etc.

A collection of contents in a psychological domain identified by the psychological domain classifier 1904 may comprise a plurality of QA pairs 1906 and/or a plurality of plain texts 1908. The QA pairs 1906 may comprise questions on psychological issues from website users and corresponding answers provided by psychologists, psychological experts, or others on websites. The plain texts 1908 may refer to various literal descriptions about psychological topics that are not in a format of QA pair.

A QA detection operation 1910 may be performed on the QA pairs 1906 so as to generate psychological data pairs. For example, questions and answers in the QA pairs 1906 may be identified and separated by html tags, and thus psychological data pairs may be formed from the QA pairs 1906. In some cases, a first data part of a generated psychological data pair may include a question in a QA pair 1906, and a second data part of the generated psychological data pair may include an answer in the QA pair 1906, thus the generated psychological data pair may also be construed as in a <Question, Answer> pair format. The generated psychological data pairs may be further appended to a psychological knowledge graph 1914.

A QA generation operation 1912 may be performed on the plain texts 1908 so as to generate psychological data pairs. Various existing approaches for generating QA pairs from plain texts may be adopted in the QA generation operation 1912. The psychological data pairs generated in the QA generation operation 1912 may be in a <Question, Answer> format. The generated psychological data pairs may be further appended to the psychological knowledge graph 1914.

As discussed above, the generated psychological data pairs in FIG. 19 may be in a <Question, Answer> format, these QA-style psychological data pairs in the psychological knowledge graph may be used by the chatbot for answering user's questions, performing psychological tests, determining cure strategies for users, etc. For example, if a question from the user matches a question in a psychological data pair, then an answer in the psychological data pair may be provided to the user as a response to the question from the user. For example, during a psychological test, if the current session is relevant to a question in a psychological data pair, then this question may be provided to the user as a further psychological question in the psychological test. For example, when determining a cure strategy, if the current session is relevant to a question in a psychological data pair and an answer in this psychological data pair is about a psychological cure opinion, then the answer in this psychological data pair may be determined as a candidate cure strategy.

It should be appreciated that, in some implementations, before appending the generated QA-style psychological data pairs to the psychological knowledge graph, expression transformation may also be applied on questions in the psychological data pairs. For example, as for an expression "Does your girlfriend care about your situation?", it may be transformed into "Does your lover care about your situation?", "Does your girlfriend pay close attention to your situation?", etc. The expression transformation may improve diversity of the psychological data pairs in the psychological knowledge graph. For example, when the chatbot is chatting with a plurality of users based on the psychological knowledge graph, the diversity of the psychological data pairs in the psychological knowledge graph may avoid usage of the same expressions to these users. Moreover, when the chatbot is conducting an implicit psychological test, the diversity of psychological questions may avoid that a user recognizes the conduction of the psychological test and thus gives imaginary or fake answers.

Figure 20:
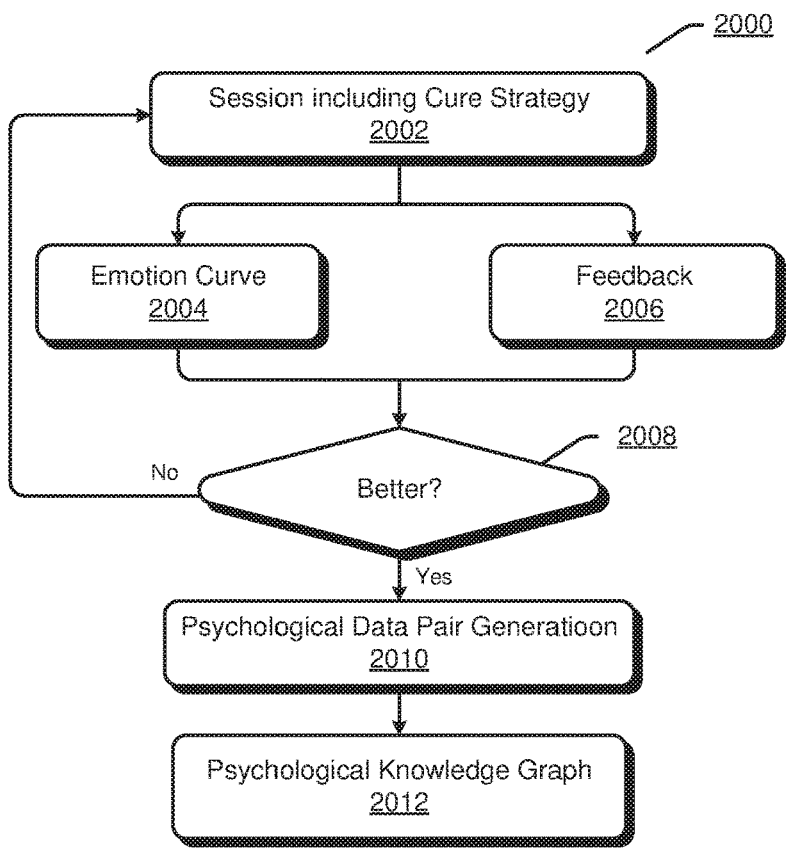
FIG. 20 illustrates an exemplary process for establishing a psychological knowledge graph according to an embodiment.

FIG. 20 illustrates an exemplary process 2000 for establishing a psychological knowledge graph according to an embodiment. The process 2000 may generate psychological data pairs from at least one session between a user and a chatbot and/or between a user and a psychologist through data mining. Herein, "session" may comprise messages and responses input by a user, a Chabot and/or a psychologist. In some implementations, a generated psychological data pair <Data 1, Data 2> in the process 2000 may also be represented in a <Session, Cure strategy> format.

At 2002, a session including a cure strategy provided by a chatbot or a psychologist may be selected, wherein the session may involve a target user.

At 2004, an emotion curve of the user may be retrieved. At 2008, it is determined whether a psychological condition of the user is getting better, through determining whether the emotion curve meets a predefined condition. For example, a predetermined threshold may be set for the emotion curve, and if a current emotion state of the user is above the threshold, it may be determined that the psychological condition of the user is getting better, i.e., the cure strategy previously provided to the user is effective. Thus, this session may be further used for generating a psychological data pair at 2010. For example, the session may be included in a first data part of the psychological data pair, and the cure strategy may be included in a second data part of the psychological data pair.

At 2006, a feedback from the user may be obtained. The feedback may be provided by the user in a chat flow between the user and the chatbot or between the user and a psychologist. At 2008, the feedback may be used for determining whether a psychological condition of the user is getting better. For example, as for the chat flow in FIG. 7, the feedback "I am feeling better now" indicates that the psychological condition of the user is getting better. Thus, this session may be further used for generating a psychological data pair at 2010. For example, at least one sentence in the session may be included in a first data part of the psychological data pair, and the cure strategy may be included in a second data part of the psychological data pair. Still taking the chat flow in FIG. 7 as an example, an exemplary generated psychological data pair may comprise a Session part of {"Feeling so bad these days", "What happened", "Work", "A tight deadline?", "Not about deadline, just judged too much by colleagues", "Oh . . . that's easy to be tired". "Yes, too tired"}, and a Cure strategy part of {"a 30-minute running for refreshing"}. Another exemplary generated psychological data pair may comprise a Session part of {"judged too much by colleagues"}, and a Cure strategy part of {"a 30-minute running for refreshing"}.

If it is determined at 2008 that the user is not getting better, the process 2000 will return to 2002.

Psychological data pairs generated at 2010 may be further appended to a psychological knowledge graph 2012.

As discussed above, the generated psychological data pairs in FIG. 20 may be in a <Session, Cure strategy> format, these psychological data pairs in the psychological knowledge graph may be used by the chatbot for, such as, determining cure strategies for users, etc. For example, when determining a cure strategy, if the current session is relevant to a Session in a psychological data pair, then a Cure strategy in this psychological data pair may be determined as a candidate cure strategy.

Figure 21:
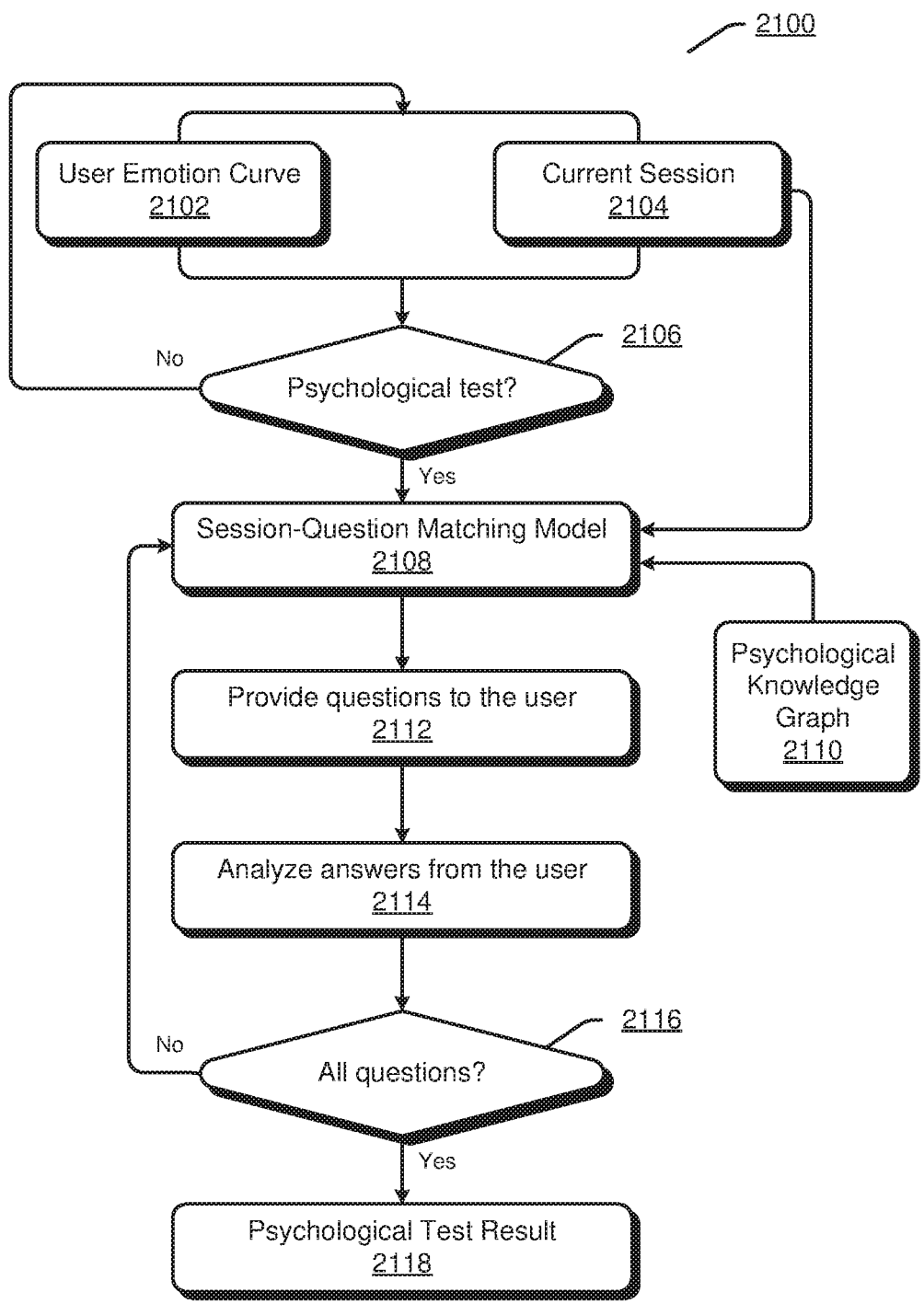
FIG. 21 illustrates an exemplary process for performing an implicit psychological test according to an embodiment.

FIG. 21 illustrates an exemplary process 2100 for performing an implicit psychological test according to an embodiment.

In some cases, the process 2100 may be triggered by an emotion curve 2102 of a user. If the current emotion state of the user is judged as below a predetermined threshold on the emotion curve, then it is determined at 2106 that an implicit psychological test may be performed.

In other cases, the process 2100 may be triggered by a current session 2104 of the user. For example, if messages input by the user in the current session is judged, through sentiment analysis, as having negative emotions, then it is determined at 2106 that an implicit psychological test may be performed.

If it is determined at 2106 that no psychological test is required to be performed, the process 2100 may return so as to further judge the emotion curve 2102 and the current session 2104.

When determining to perform an implicit psychological test, a session-question matching model may be used at 2108 for determining psychological questions in the implicit psychological test based at least on the current session 2104 and a psychological knowledge graph 2110.

Taking the chat flow in FIG. 7 as an example, when the user inputs "Feeling so sad these days", the current session may be denoted as: Session 1="User: Feeling so sad these days". A question "What happened?" may be determined by the session-question matching model as a psychological question in the psychological test. When the user inputs "Work", the current session may be updated as: Session 2="User: Feeling so sad these days; Chatbot: What happened?; User: Work", A further question "A tight deadline?" may be determined by the session-question matching model as a further psychological question in the psychological test.

As discussed above, the session-question matching model may decide which question to be shown to the user, so as to further capture the user's opinion or answer for psychological condition detecting.

A gradient-boosting decision tree (GBDT) may be adopted in the session-question matching model to compute similarity scores between the current session 2104 and questions in psychological data pairs in the psychological knowledge graph 2110, wherein these psychological data pairs may be QA-style psychological data pairs, and questions in the psychological data pairs may also be referred to as candidate questions.

In an implementation, a feature in the GBDT may be based on a language model for information retrieval. This feature may evaluate relevance between a candidate question q and a current session Q through:

$$P(q|Q)=\Pi_{w \in q}[(1-\lambda)P_{ml}(w|Q)+\lambda P_{ml}(w|C)] \quad \text{Equation (10)}$$

where $P_{ml}(w|Q)$ is the maximum likelihood of word w estimated from Q, and $P_{ml}(w|C)$ is a smoothing item that is computed as the maximum likelihood estimation in a large-scale corpus C. The smoothing item avoids zero probability, which stems from those words appearing in the candidate question q but not in the current session Q. $\lambda$ is a parameter that acts as a trade-off between the likelihood and the smoothing item, where $\lambda \in [0, 1]$. This feature works well when there are a number of words overlapped between the candidate question and the current session.

In an implementation, a feature in the GBDT may be based on a translation-based language model. This feature may learn word-to-word and/or phrase-to-phrase translation probability from, such as, candidate questions, and may incorporate the learned information into the maximum likelihood. Given a candidate question q and a current session Q, the translation-based language model may be defined as:

$$P_{tr \cdot b}(q|Q)=\Pi_{w \in q}[(1-\lambda)P_{mx}(w|Q)+\lambda P_{ml}(w|C)] \quad \text{Equation (11)}$$

$$\text{where } P_{mx}(w|Q)=\alpha P_{ml}(w|Q)+\beta P_{tr}(w|Q) \quad \text{Equation (12)}$$

$$P_{tr}(w|Q)=\Sigma_{v \in Q}P_{tp}(w|v)P_{ml}(v|Q) \quad \text{Equation (13)}$$

Here $\lambda$, $\alpha$ and $\beta$ are parameters satisfying $\lambda \in [0, 1]$ and $\alpha+\beta=1$. $P_{tp}(w|v)$ is a translation probability from word v in Q to word w in q. $P_{tr}(.)$, $P_{mx}(.)$ and $P_{trb}(.)$ are similarity functions constructed step-by-step by using $P_{tp}(.)$ and $P_{ml}(.)$.

In an implementation, a feature in the GBDT may be an edit distance between a candidate question and a current session in a word or character level.

In an implementation, a feature in the GBDT may be a maximum subsequence ratio between a candidate question and a current session.

In an implementation, a feature in the GBDT may be a cosine similarity score from a RNN using GRUB. The cosine similarity score may be an evaluation for similarity between a candidate question and a current session. The candidate question and the current session may be input into a respective RNN-GRU layer so as to obtain corresponding dense vectors. The dense vectors may be further used for determining a similarity score between the candidate question and the current session.

Through the session-question matching model, one or more psychological questions may be determined for the psychological test. At 2112, the psychological questions may be provided to the user.

At 2114, answers from the user may be analyzed. For example, a sentiment analysis process according to the embodiments of the present disclosure may be applied on the answers from the user, so as to detect the user's current psychological condition or emotion state.

At 2116, it may be determined whether all psychological questions in the psychological test have been sent to the user. If not, the process 2100 may return to 2108. If yes, a psychological test result may be generated at 2118. The psychological test result may be in various forms, such as, the result 500 shown in FIG. 5, an emotion curve 1700 shown in FIG. 17, etc.

It should be appreciated that, although not shown in FIG. 21, there may be a test control strategy included in the process 2100. For example, if there are a lot of psychological questions needed to be sent to the user so as to obtain a final result, the process 2100 may record questions that the user has answered, questions remaining to be sent to the user, and time duration of the psychological test having be conducted. Thus, the whole psychological test may be conducted in several parts in two or more sessions, rather than conducted at a time.

Figure 22:
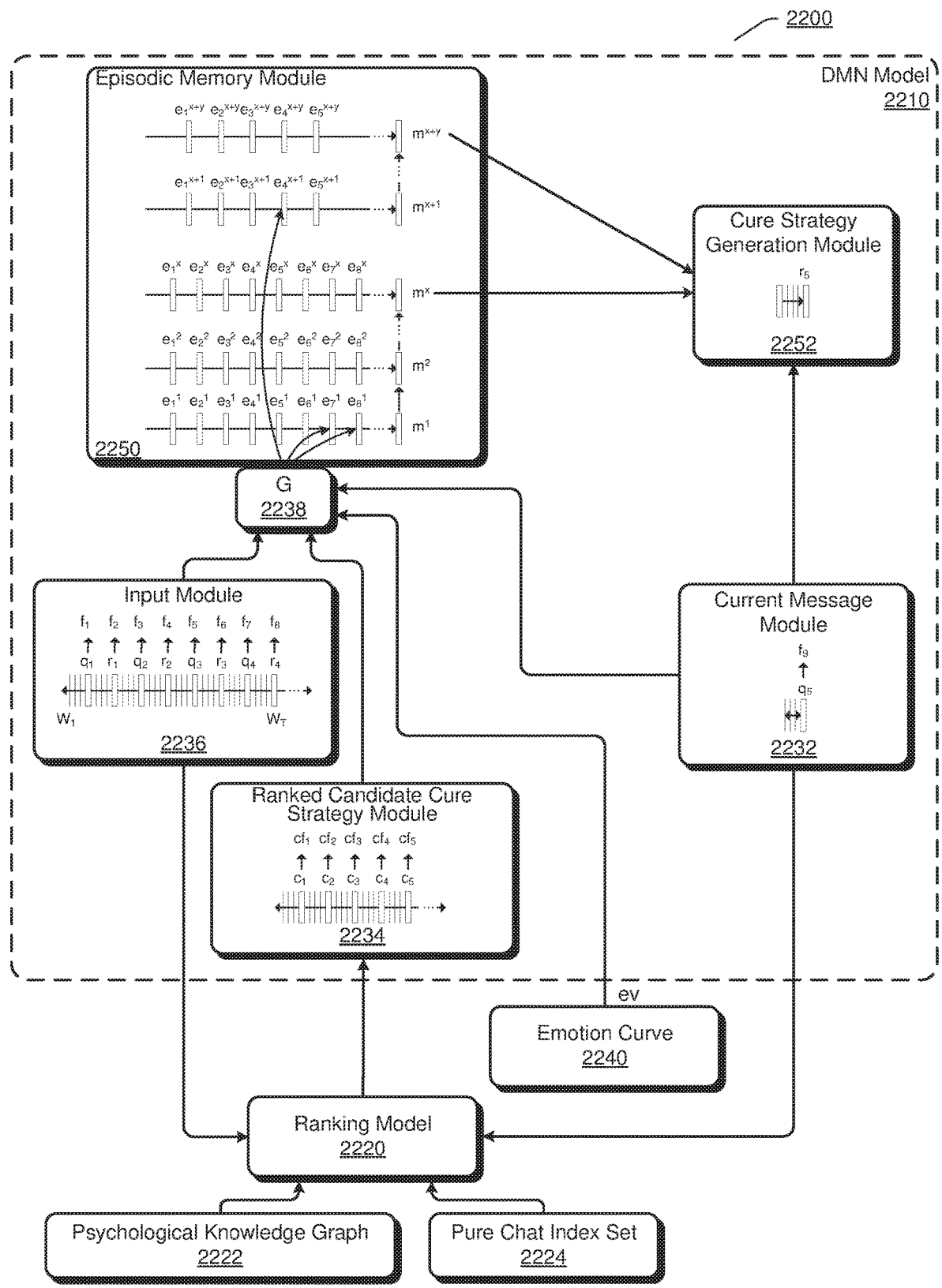
FIG. 22 illustrates an exemplary process for generating a cure strategy through a Dynamic Memory Network (DMN) model according to an embodiment.

FIG. 22 illustrates an exemplary process 2200 for generating a cure strategy through a DMN model according to an embodiment. As discussed above, a DMN-based reasoning framework may be used by the chatbot for generating a cure strategy that is to be provided to a user or a psychologist.

As shown in FIG. 22, a DMN model 2210 may be used for generating a cure strategy in a word-by-word approach. The DMN model 2210 may cooperate with a ranking model 2220 which can determine one or more candidate cure strategies to be used by the DMN model 2210 to generate a cure strategy. However, it should be appreciated that, in other implementations, the ranking model 2220 may also be omitted from the process 2200.

The DMN model 2210 may take a current message as an input. The current message is currently input by the user and may be construed as a trigger of the process 2200. For example, a current message $q_5$ may be input through a current message module 2232.

The DMN model 2210 may take a selected session between the user and the chatbot or between the user and the psychologist as an input. The selected session may be the current session, one or more of historical sessions, a part of a historical session, etc. Preferably, the selected session may be determined as a session that is relevant to the current message. The selected session may comprise a set of messages and responses between two participants in a chat flow. The number of messages and responses in the selected session may be controlled by a predefined window. The selected session may include important information about the user that can contribute to generate an appropriate cure strategy for the user. For example, four messages $q_2$, $q_3$, $q_4$ and four corresponding responses $r_1$, $r_2$, $r_3$, $r_4$ in the selected session may be input through an input module 2236.

The DMN model 2210 may take one or more ranked candidate cure strategies $C_1$ to $C_5$ as inputs, which are determined by the ranking model 2220. In an implementation, the ranking model 2220 may be used for determining one or more candidate cure strategies from a psychological knowledge graph 2222 and/or a pure chat index set 2224. For example, as discussed above, the psychological knowledge graph 2222 may comprise psychological data pairs in a <Session, Cure strategy> format, and the cure strategies in these psychological data pairs may be referred to as candidate cure strategies. In an implementation, the ranking model 2220 may be a learning-to-rank model, and may adopt a GBDT to determine relevance scores between the current message $q_5$ and the candidate cure strategies, and rank the candidate cure strategies based on the scores. One or more top-ranked candidate cure strategies may be output by the ranking model 2220.

Alternatively, the DMN model 2210 may take an emotion curve of the user as an input. The emotion curve may be projected into an emotion vector ev and then input to the DMN model 2210.

Next, exemplary processes in modules of the DMN model 2210 will be discussed in details.

At the input module 2236, a sequence of sentences ($q_1$, $r_1$, $q_2$, $r_2$, $q_3$, $r_3$, $q_4$, $r_4$ in the selected session may be processed. Each sentence is ended with "</s>" to denote the ending of one sentence. All the eight sentences may be concatenated together to form a word sequence having T words, from $W_1$ to $W_T$. A bidirectional GRU encoding may be applied on the word sequence. For the left-to-right direction or the right-to-left direction, at each time step t, the DMN model 2210 may update its hidden state as $h_t$=GRU(L[$w_t$], $h_{t-1}$), where L is an embedding matrix, and $w_t$ is a word index of the t-th word in the word sequence. Thus, a resulting representation vector for a sentence is a combination of two vectors and each vector is from one direction. Internal mechanism of the GRU may follow Equations (1) to (4). These equations may also be abbreviated as $h_t$=GRU($x_t$, $h_{t-1}$).

In addition to encoding the word sequence, a positional encoding with bidirectional GRU may also be applied so as to represent "facts" of the sentences. The facts may be computed as $f_t$=GRU$_{l2r}$(L[$S_t$], $f_{t-1}$)+GRU$_{r2l}$(L[$S_t$], $f_{t-1}$), where l2r denotes left-to-right, r2l denotes right-to-left, $S_t$ is an embedding expression of a current sentence, and $f_{t-1}$, $f_t$ are facts of a former sentence and the current sentence respectively. As shown in FIG. 22, facts $f_1$ to $f_8$ are obtained for the eight sentences in the selection session.

At the current message module 2232, the encoding for the current message $q_5$ is a simplified version of the input module 2236, where there is only one sentence to be processed in the current message module 2232. The processing by the current message module 2232 is similar with the input module 2236. Assuming that there are $T_Q$ words in the current message, hidden states at the time step t may be computed as $q_t$=[GRU$_{l2r}$(L[$W_t^Q$], $q_{t-1}$), GRU$_{r2l}$(L[$W_t^Q$], $q_{t-1}$)], where L is an embedding matrix, and $W_t^Q$ is a word index of the t-th word in the current message. A fact $f_9$ may be obtained for the current message $q_5$ in the current message module 2232.

The DMN model 2210 may comprise a ranked candidate cure strategy module 2234. At the ranked candidate cure strategy module 2234, the DMN model 2210 may compute hidden state and facts for one or more ranked candidate cure strategies in the same way as the input module 2236. As an example, FIG. 22 shows five candidate cure strategies $C_1$ to $C_5$, and five facts $cf_1$ to $cf_5$ are obtained for these candidate cure strategies.

Although not shown, the DMN model 2210 may also compute a fact $f_{ev}$ for the emotion vector in the same way as the current message module 2232.

The DMN model 2210 may comprise an attention mechanism module and an episodic memory module. The episodic memory module may include a recurrent network, and the attention mechanism module may be based on a gating function. The attention mechanism module may be separated from or incorporated in the episodic memory module.

According to a conventional computing process, the episodic memory module and the attention mechanism module may cooperate to update episodic memory in an iteration way. For each pass i, the gating function of the attention mechanism module may take a fact $f^i$, a previous memory vector $m^{i-}$, and a current message S as inputs, to compute an attention gate $g_t^i = G[f^i, m^{i-1}, S]$. To compute the episode $e^i$ for pass i, a GRU over a sequence of inputs, e.g., a list of facts $f^i$ weighted by the gates $g^i$ may be applied. Then the episodic memory vector may be computed as $m^i = GRU(e^i, m^{i-1})$. Initially, $m^0$ is equal to a vector expression of the current message S. The episode vector that is given to a generation module may be the final state $m^x$ of the GRU. The following Equation (14) is for updating hidden states of the GRU at a time step t, and the following Equation (15) is for computing the episode.

$$h_t^i = g_t^i GRU(f_t, h_{t-1}^i) + (1-g_t^i)h_{t-1}^i \qquad \text{Equation (14)}$$

$$e^i = h_{T_C}^i \qquad \text{Equation (15)}$$

where $T_C$ is the number of input sentences.

However, according to the embodiment of the present disclosure, the processing in an attention mechanism module 2238 and an episodic memory module 2250 in the DMN model 2210 may further take the ranked candidate cure strategies and/or the emotion curve into account. As shown in FIG. 22, besides the input module 2236 and the current message module 2232, the attention mechanism module 2238 also obtains inputs from the ranked candidate cure strategy module 2234 and the emotion curve 2240. Thus, the attention gate may be computed as, e.g., $g_t^i = G[f^i, m^{i-1}, f_9, cf^i, f_{ev}, m^{x+i-1}]$, where $cf^i$ denotes the facts from the ranked candidate cure strategies, and $m^{x+i-1}$ is a memory vector computed for the ranked candidate cure strategies. Accordingly, the recurrent network in the episodic memory module 2250 further comprises a computing process of memories $m^{x+1}$ to $m^{x+y}$ for the ranked candidate cure strategies. For example, $e_1^{x+i}$ to $e_5^{x+i}$ in FIG. 22 may correspond to the ranked candidate cure strategies. Outputs from the episodic memory module 2250 to the cure strategy generation module 2252 may include at least $m^x$ and $m^{x+y}$.

The cure strategy generation module 2252 may be used for generating a cure strategy. A GRU decoder may be adopted in the cure strategy generation module 2252, and an initial state of the GRU decoder may be initialized to be the last memory vector $a_0 = [m^x, m^{x+y}]$. At a time step t, the GRU decoder may take the current message $f_9$, a last hidden state $a_{t-1}$, and a previous output $y_{t-1}$ as inputs, and then compute a current output as:

$$y_t = \text{softmax}(W^{(a)} a_t) \qquad \text{Equation (16)}$$

where $a_t = GRU([y_{t-1}, f_9], a_{t-1})$, and $W^{(a)}$ is a weight matrix by training.

The last generated word may be concatenated to the cure strategy vector at each time step. The generated output by the cure strategy generation module 2252 may be trained with a cross-entropy error classification of a correct sequence attached with a "</s>" tag at the end of the sequence.

The generated cure strategy output from the cure strategy generation module 2252 may be further provided to the user or the psychologist.

It should be appreciated that all the modules, equations, parameters and processes discussed above in connection with FIG. 22 are exemplary, and the embodiments of the present disclosure are not limited to any details in the discussion.

Moreover, although not shown in FIG. 22, there may be, a feedback mechanism included in the process 2200. For example, a feedback from the user may be obtained after the generated cure strategy is provided to the user. If the feedback is positive, e.g., the cure strategy is effective, a <selected session+current message, cure strategy> pair may be appended to the psychological knowledge graph 2222 as a new psychological data pair. A first data part of the new psychological data pair is a combination of the selected session processed in the input module 2236 and the current message processed in the current message module 2232, and a second data part of the new psychological data pair is the cure strategy generated in the cure strategy generation module 2252. In this way, the psychological knowledge graph 2222 may be updated dynamically.

Figure 23:
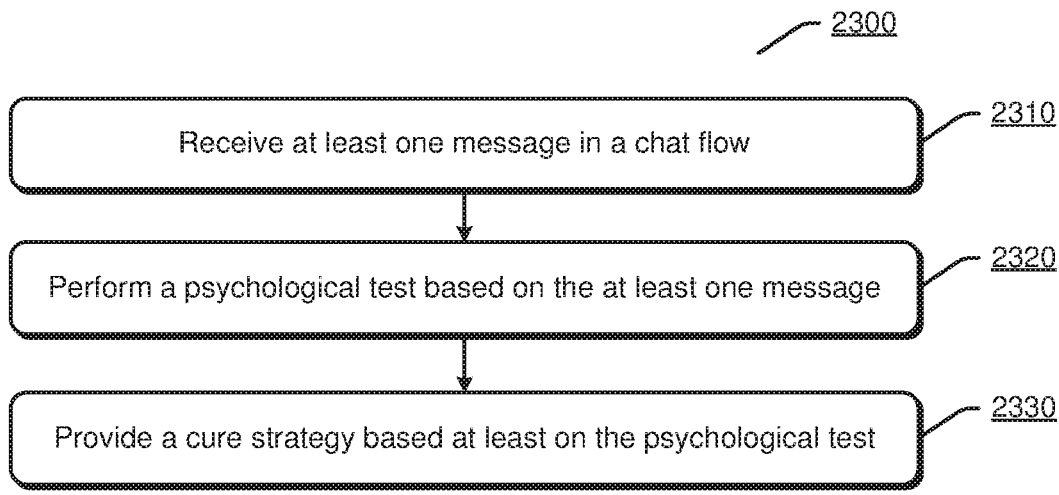
FIG. 23 illustrates a flowchart of an exemplary method for assisting psychological cure in automated chatting according to an embodiment.

FIG. 23 illustrates a flowchart of an exemplary method 2300 for assisting psychological cure in automated chatting according to an embodiment. The method 2300 may be implemented when a chatbot is chatting with a user.

At 2310, at least one message may be received in a chat flow.

At 2320, a psychological test may be performed based on the at least one message.

At 2330, a cure strategy may be provided based at least on the psychological test.

In an implementation, the psychological test may be performed implicitly in the chat flow. The performing the psychological test may comprise: selecting at least one question from a psychological knowledge graph established through data mining; providing the at least one question in the chat flow; and receiving at least one answer to the at least one question in the chat flow. The psychological knowledge graph may be established from at least one of: plain texts or question-answer pairs in a psychological domain on at least one website; and at least one session between a user and a chatbot and/or between the user and a psychologist. The at least one question may be selected through matching between a current session and questions in the psychological knowledge graph.

In an implementation, the performing the psychological test may comprise: performing sentiment analysis on the at least one message, the at least one message being in at least one format of text, voice, image and video, the sentiment analysis being for classifying the at least one message into one of a plurality of emotion categories.

In an implementation, before performing the psychological test, the method 2300 may further comprise at least one of: determining that the at least one message includes a request for the psychological test; determining that the at least one message indicates a negative emotion; and determining that an emotion curve of a user meets a predefined condition, the emotion curve being formed from emotion states of the user within a time period.

In an implementation, the providing the cure strategy may comprise: establishing, in the chat flow, a session connection between a user and a psychologist, the cure strategy being provided through the session connection.

In an implementation, the providing the cure strategy may comprise determining the cure strategy through DMN-based reasoning, and the DMN-based reasoning may be based on at least one of: at least one candidate cure strategy determined from a psychological knowledge graph; an emotion curve of a user; and a session between the user and a chatbot and/or between the user and a psychologist.

In an implementation, the method 2300 may further comprise: providing a result of the psychological test in the chat flow.

In an implementation, the method 2300 may further comprise: receiving a request for obtaining an emotion curve; and providing the emotion curve based on the request.

In an implementation, the method 2300 may further comprise: receiving a feedback for the cure strategy; if the feedback is positive, generating a psychological data pair which includes a current session in a first data part and includes the cure strategy in a second data part; and appending the psychological data pair to a psychological knowledge graph.

In an implementation, the method 2300 may further comprise: receiving a feedback for the cure strategy; and if the feedback is positive, generating an emotion card which includes information about at least one of topic, emotion, time period, reason, cure strategy, and effectiveness.

It should be appreciated that the method 2300 may further comprise any steps/processes for assisting psychological cure in automated chatting according to the embodiments of the present disclosure as mentioned above.

Figure 24:
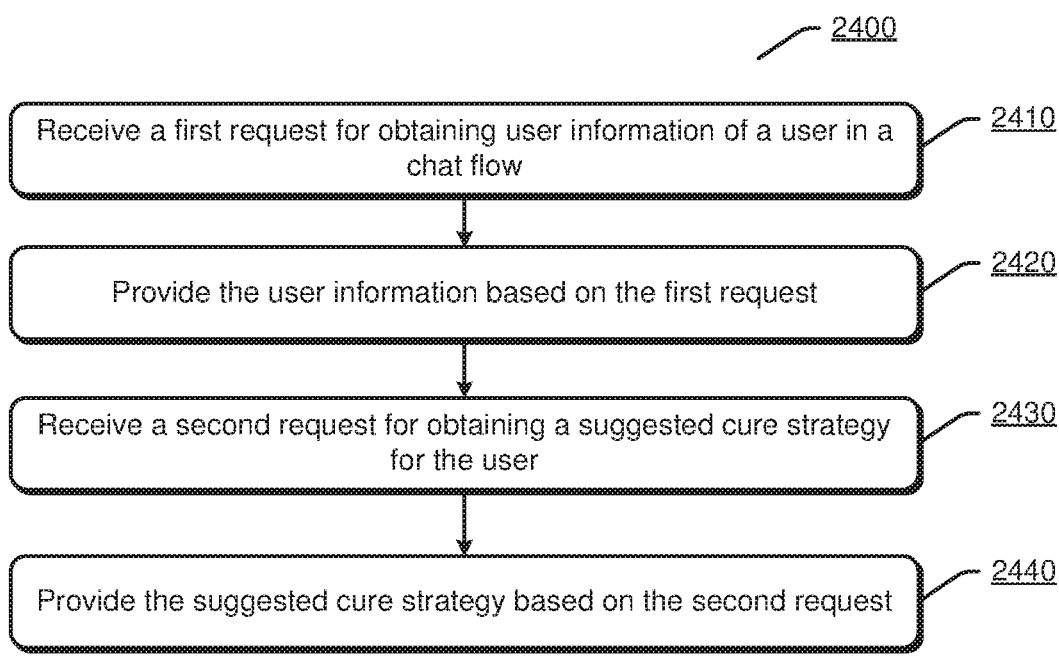
FIG. 24 illustrates a flowchart of an exemplary method for assisting psychological cure in automated chatting according to an embodiment.

FIG. 24 illustrates a flowchart of an exemplary method 2400 for assisting psychological cure in automated chatting according to an embodiment. The method 2400 may be implemented when a chatbot is chatting with a psychologist.

At 2410, a first request for obtaining user information of a user may be received in a chat flow.

At 2420, the user information may be provided based on the first request.

At 2430, a second request for obtaining a suggested cure strategy for the user may be received.

At 2440, the suggested cure strategy may be provided based on the second request, wherein the suggested cure strategy may be determined based at least on the user information.

In an implementation, the user information may comprise at least one of: an emotion card of the user, including information about at least one of topic, emotion, time period, reason, cure strategy, and effectiveness; an emotion curve of the user, being formed from emotion states of the user within a time period; and a result of a psychological test taken by the user.

In an implementation, the method 2400 may further comprise: establishing, in the chat flow, a session connection between the user and a psychologist.

It should be appreciated that the method 2400 may further comprise any steps/processes for assisting psychological cure in automated chatting according to the embodiments of the present disclosure as mentioned above.

Figure 25:
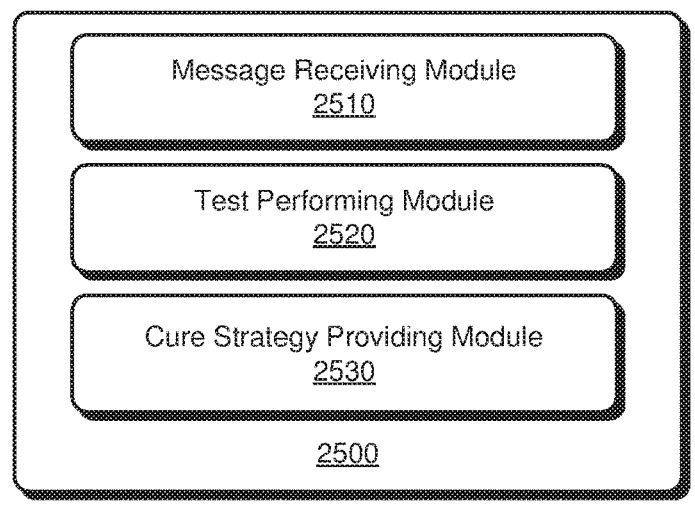
FIG. 25 illustrates an exemplary apparatus for assisting psychological cure in automated chatting according to an embodiment.

FIG. 25 illustrates an exemplary apparatus 2500 for assisting psychological cure in automated chatting according to an embodiment.

The apparatus 2500 may comprise: a message receiving module 2510, for receiving at least one message in a chat flow; a test performing module 2520, for performing a psychological test based on the at least one message; and a cure strategy providing module 2530, for providing a cure strategy based at least on the psychological test.

In an implementation, the psychological test may be performed implicitly in the chat flow. The test performing module 2520 may comprise: a question selecting module, for selecting at least one question from a psychological knowledge graph established through data mining; a question providing module, for providing the at least one question in the chat flow; and an answer receiving module, for receiving at least one answer to the at least one question in the chat flow.

In an implementation, the cure strategy providing module 2530 may comprise: a session connection establishing module, for establishing, in the chat flow, a session connection between a user and a psychologist, the cure strategy being provided through the session connection.

In an implementation, the cure strategy providing module 2530 may be for determining the cure strategy through DMN-based reasoning. The DMN-based reasoning may be based on at least one of: at least one candidate cure strategy determined from a psychological knowledge graph; an emotion curve of a user; and a session between the user and a chatbot and/or between the user and a psychologist.

Moreover, the apparatus 2500 may also comprise any other modules configured for assisting psychological cure in automated chatting according to the embodiments of the present disclosure as mentioned above.

Figure 26:
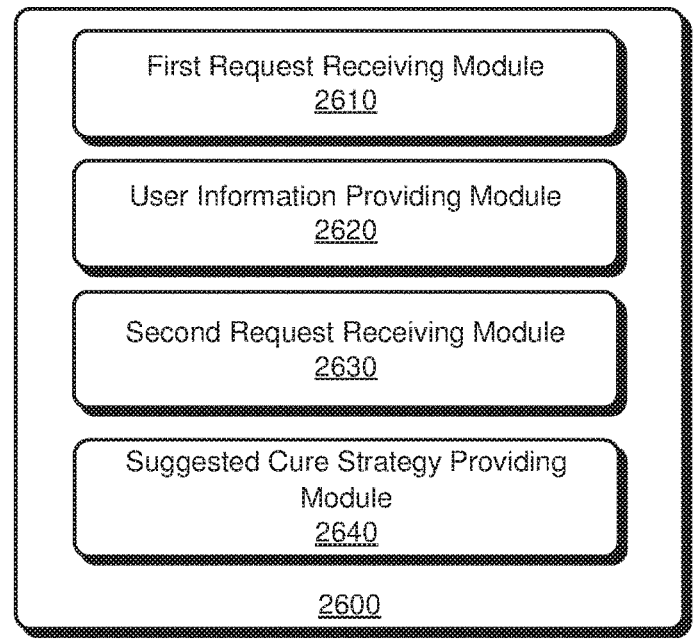
FIG. 26 illustrates an exemplary apparatus for assisting psychological cure in automated chatting according to an embodiment.

FIG. 26 illustrates an exemplary apparatus 2600 for assisting psychological cure in automated chatting according to an embodiment.

The apparatus 2600 may comprise: a first request receiving module 2610, for receiving a first request for obtaining user information of a user in a chat flow; a user information providing module 2620, for providing the user information based on the first request; a second request receiving module 2630, for receiving a second request for obtaining a suggested cure strategy for the user; and a suggested cure strategy providing module 2640, for providing the suggested cure strategy based on the second request, the suggested cure strategy being determined based at least on the user information.

Moreover, the apparatus 2600 may also comprise any other modules configured for assisting psychological cure in automated chatting according to the embodiments of the present disclosure as mentioned above.

Figure 27:
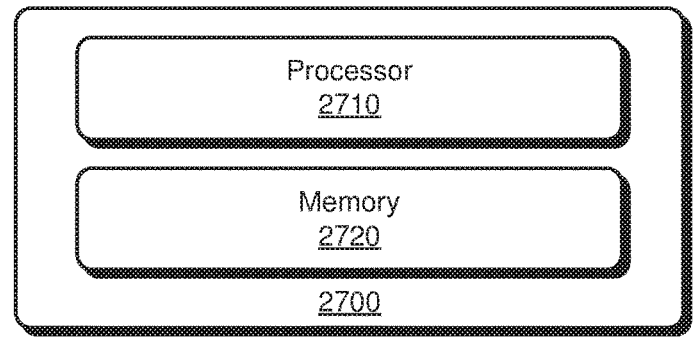
FIG. 27 illustrates an exemplary apparatus for assisting psychological cure in automated chatting according to an embodiment.

FIG. 27 illustrates an exemplary apparatus 2700 for assisting psychological cure in automated chatting according to an embodiment.

The apparatus 2700 may comprise at least one processor 2710. The apparatus 2700 may further comprise a memory 2720 that is connected with the processor 2710. The memory 2720 may store computer-executable instructions that, when executed, cause the processor 2710 to perform any operations of the methods for assisting psychological cure in automated chatting according to the embodiments of the present disclosure as mentioned above.

The embodiments of the present disclosure may be embodied in a non-transitory computer-readable medium. The non-transitory computer-readable medium may comprise instructions that, when executed, cause one or more processors to perform any operations of the methods for assisting psychological cure in automated chatting according to the embodiments of the present disclosure as mentioned above.

It should be appreciated that all the operations in the methods described above are merely exemplary, and the present disclosure is not limited to any operations in the methods or sequence orders of these operations, and should cover all other equivalents under the same or similar concepts.

It should also be appreciated that all the modules in the apparatuses described above may be implemented in various approaches. These modules may be implemented as hardware, software, or a combination thereof. Moreover, any of these modules may be further functionally divided into sub-modules or combined together.

Processors have been described in connection with various apparatuses and methods. These processors may be implemented using electronic hardware, computer software, or any combination thereof. Whether such processors are implemented as hardware or software will depend upon the particular application and overall design constraints imposed on the system. By way of example, a processor, any portion of a processor, or any combination of processors presented in the present disclosure may be implemented with a microprocessor, microcontroller, digital signal processor (DSP), a field-programmable gate array (FPGA), a programmable logic device (PLD), a state machine, gated logic, discrete hardware circuits, and other suitable processing components configured to perform the various functions described throughout the present disclosure. The functionality of a processor, any portion of a processor, or any combination of processors presented in the present disclosure may be implemented with software being executed by a microprocessor, microcontroller, DSP, or other suitable platform.

Software shall be construed broadly to mean instructions, instruction sets, code, code segments, program code, programs, subprograms, software modules, applications, software applications, software packages, routines, subroutines, objects, threads of execution, procedures, functions, etc. The software may reside on a computer-readable medium. A computer-readable medium may include, by way of example, memory such as a magnetic storage device (e.g., hard disk, floppy disk, magnetic strip), an optical disk, a smart card, a flash memory device, random access memory (RAM), read only memory (ROM), programmable ROM (PROM), erasable PROM (EPROM), electrically erasable PROM (EEPROM), a register, or a removable disk. Although memory is shown separate from the processors in the various aspects presented throughout the present disclosure, the memory may be internal to the processors (e.g., cache or register).

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein. All structural and functional equivalents to the elements of the various aspects described throughout the present disclosure that are known or later come to be known to those of ordinary skill in the art are expressly incorporated herein by reference and are intended to be encompassed by the claims.

What is claimed is:

1. A method for assisting in providing a psychological response within an automated chat, said method comprising:
receiving, by a chatbot and from a user, at least one message in a chat flow;
performing, by the chatbot, an automated psychological test based on the at least one message, wherein the automated psychological test is implicitly performed by the chatbot based on a user emotion indicated by the at least one message,
wherein implicitly performing the automated psychological test based on the user emotion includes:
generating a sequence of responses;
for each response in the sequence of responses, determining a corresponding time-delay setting, wherein each time-delay setting is designed to impose a time delay after either (i) a response provided by the chatbot or (ii) a response provided by the user, and wherein each time-delay setting is designed to delay when a subsequent response provided by the chatbot is delivered to the user such that the delay further facilitates an objective of the chatbot to elicit a true response from the user, where that true response accurately reflects an emotion of the user; and
after either (i) the response provided by the chatbot or (ii) the response provided by the user, impose a particular time delay such that the subsequent response provided by the chatbot is delivered to the user only after the particular time delay elapses; and
wherein the automated psychological test includes:
determining the user emotion based on a first machine-learning model trained over a neural network using training data that includes at least one of text data, voice data, image data, or video data;
generating an emotion curve within a time period; and
determining one or more values of one or more factors associated with a stress of the user based on the emotion curve;
providing, by the chatbot, a cure strategy designed to reduce the user emotion or the stress, wherein the cure strategy is designed based on the automated psychological test, and wherein the cure strategy is determined via a second machine-learning model that is trained over a dynamic memory network using training data, where the training data includes psychological data pairs.

2. The method of claim 1, wherein initiating the psychological test implicitly comprises providing the psychological test automatically without an explicit request by the user to initiate the psychological test, and the performing the psychological test comprises:
selecting at least one question from a psychological knowledge graph established through data mining;
providing the at least one question in the chat flow; and
receiving at least one answer to the at least one question in the chat flow.

3. The method of claim 2, wherein the psychological knowledge graph is established from at least one of:
plain texts or question-answer pairs in a psychological domain on at least one website; and
at least one session between a user and a chatbot and/or between the user and a psychologist.

4. The method of claim 2, wherein the at least one question is selected through matching between a current session and questions in the psychological knowledge graph.

5. The method of claim 1, wherein the performing the psychological test comprises:
performing sentiment analysis on the at least one message, the at least one message being in at least one format of text, voice, image and video, the sentiment analysis being for classifying the at least one message into one of a plurality of emotion categories.

6. The method of claim 1, before performing the psychological test, further comprising at least one of:
determining that the at least one message includes a request for the psychological test;
determining that the at least one message indicates a negative emotion; and
determining that the emotion curve of a user meets a predefined condition, the emotion curve being formed from emotion states of the user within a time period.

7. The method of claim 1, wherein the providing the cure strategy comprises:
establishing, in the chat flow, a session connection between a user and a psychologist, the cure strategy being provided through the session connection.

8. The method of claim 1, wherein the providing the cure strategy comprises determining the cure strategy based on at least one of:
at least one candidate cure strategy determined from a psychological knowledge graph;

the emotion curve of a user; and
a session between the user and a chatbot and/or between the user and a psychologist.

9. The method of claim 1, further comprising:
providing a result of the psychological test in the chat flow.

10. The method of claim 1, further comprising:
receiving a request for obtaining the emotion curve; and
providing the emotion curve based on the request.

11. The method of claim 1, further comprising:
receiving a feedback for the cure strategy;
if the feedback is positive, generating a psychological data pair which includes a current session in a first data part and includes the cure strategy in a second data part; and
appending the psychological data pair to a psychological knowledge graph.

12. The method of claim 1, further comprising:
receiving a feedback for the cure strategy; and
if the feedback is positive, generating an emotion card which includes information about at least one of: topic, emotion, time period, reason, cure strategy, and effectiveness.

13. A method for assisting in providing a psychological response within an automated chat, said method comprising:
receiving, by an automated chatbot, a first request for obtaining user information of a user in a chat flow;
providing the user information to a psychologist based on the first request, wherein the user information comprises results of a psychological test provided to the user, the psychological test being implicitly performed based on a user emotion detected for the user,
wherein implicitly performing the automated psychological test based on the user emotion includes:
generating a sequence of responses;
for each response in the sequence of responses, determining a corresponding time-delay setting, wherein each time-delay setting is designed to impose a time delay after either (i) a response provided by the chatbot or (ii) a response provided by the user, and wherein each time-delay setting is designed to delay when a subsequent response provided by the chatbot is delivered to the user such that the delay further facilitates an objective of the chatbot to elicit a true response from the user, where that true response accurately reflects an emotion of the user; and
after either (i) the response provided by the chatbot or (ii) the response provided by the user, impose a particular time delay such that the subsequent response provided by the chatbot is delivered to the user only after the particular time delay elapses; and
wherein implicitly initiating the psychological test includes:
determining the user emotion based on a first machine-learning model trained over a neural network using training data including at least one of text data, voice data, image data, or video data;
generating an emotion curve within a time period; and
determining one or more values of one or more factors associated with user stress based on the emotion curve;
receiving, by the chatbot, a second request for obtaining a suggested cure strategy for the user; and
providing the suggested cure strategy to the psychologist, based on the second request, the suggested cure strategy being determined based at least on the psychological test, providing the cure strategy including determining the cure strategy via a second machine-learning model trained over a dynamic memory network using training data including psychological data pairs.

14. The method of claim 13, wherein the user information comprises at least one of:
an emotion card of the user, the emotion card including information about at least one of topic, emotion, time period, reason, cure strategy, and effectiveness;
the emotion curve of the user, being formed from emotion states of the user within a time period; and
a result of a psychological test taken by the user.

15. The method of claim 13, further comprising:
establishing, in the chat flow, a session connection between the user and the psychologist.

16. An apparatus for assisting in providing a psychological cure in an automated chatting session, the apparatus comprising:
one or more processors; and
memory coupled to the one or more processor, the memory comprising computer executable instructions that are executable by the one or more processors to cause the apparatus to:
receive, by a chatbot and from a user, at least one message in a chat flow;
perform, by the chatbot, an automated psychological test based on the at least one message, wherein the automated psychological test is implicitly performed based on a user emotion indicated by the at least one message,
wherein implicitly performing the automated psychological test based on the user emotion includes:
generating a sequence of responses;
for each response in the sequence of responses, determining a corresponding time-delay setting, wherein each time-delay setting is designed to impose a time delay after either (i) a response provided by the chatbot or (ii) a response provided by the user, and wherein each time-delay setting is designed to delay when a subsequent response provided by the chatbot is delivered to the user such that the delay further facilitates an objective of the chatbot to elicit a true response from the user, where that true response accurately reflects an emotion of the user; and
after either (i) the response provided by the chatbot or (ii) the response provided by the user, impose a particular time delay such that the subsequent response provided by the chatbot is delivered to the user only after the particular time delay elapses; and
wherein the automated psychological test including:
determining the user emotion based on a first machine-learning model trained over a neural network using training data including at least one of text data, voice data, image data, or video data;
generating an emotion curve within a time period; and
determining one or more values of one or more factors associated with user stress based on the emotion curve; and
provide, by the chatbot, a cure strategy for reducing the user emotion or stress based at least on the psychological test, providing the cure strategy including determining the cure strategy via a second machine-learning model trained over a dynamic memory network using training data including psychological data pairs.

17. The apparatus of claim 16, wherein initiating the psychological test implicitly comprises:
   selecting at least one question from a psychological knowledge graph established through data mining;
   providing the at least one question in the chat flow; and
   receiving at least one answer to the at least one question in the chat flow.

18. The apparatus of claim 16, wherein the cure strategy comprises establishing, in the chat flow, a session connection between the user and a psychologist, the cure strategy being provided through the session connection.

19. The apparatus of claim 16, wherein the cure strategy is determined is based on at least one of:
   at least one candidate cure strategy determined from a psychological knowledge graph;
   the emotion curve of a user; and
   a session between the user and a chatbot and/or between the user and a psychologist.

20. The apparatus of claim 16, wherein the user emotion is determined using a sentiment analysis classifier configured to project user inputs into one or more vectors and classify the user inputs into one or more emotion categories.

\* \* \* \* \*